United States Patent [19]

Stokbroekx et al.

[11] Patent Number: 5,292,738
[45] Date of Patent: Mar. 8, 1994

[54] ANTI-VIRALLY ACTIVE PYRIDAZINAMINES

[75] Inventors: Raymond A. Stokbroekx, Beerse; Marcel J. M. Van der Aa, Kasterlee; Joannes J. M. Willems, Oud-Turnhout; Marcel G. M. Luyckx, Geel, all of Belgium

[73] Assignee: Janssen Pharmaceutica N.V., Beerse, Belgium

[21] Appl. No.: 929,622

[22] Filed: Aug. 13, 1992

Related U.S. Application Data

[60] Division of Ser. No. 637,091, Jan. 3, 1991, Pat. No. 5,157,035, which is a division of Ser. No. 702,772, Feb. 15, 1985, Pat. No. 5,001,125, which is a continuation-in-part of Ser. No. 593,444, Mar. 26, 1984, abandoned.

[51] Int. Cl.$^5$ .............................. C07D 237/06
[52] U.S. Cl. ................... 514/252; 514/212; 514/253; 540/598; 544/238
[58] Field of Search ............. 544/238, 114; 514/212, 514/236.5, 252, 253; 540/598

[56] References Cited

U.S. PATENT DOCUMENTS

| | | | |
|---|---|---|---|
| 3,753,988 | 8/1973 | Rodway | 544/237 |
| 4,110,450 | 8/1978 | Barreau | 544/238 |
| 4,399,137 | 8/1983 | Steiner et al. | 544/238 |
| 4,624,952 | 11/1986 | Biziere | 544/238 |
| 4,710,499 | 12/1987 | Wermoth et al. | 544/238 |
| 4,956,351 | 11/1990 | Mesens et al. | 544/238 |
| 5,001,125 | 3/1991 | Stokbroekx et al. | 544/238 |
| 5,112,825 | 5/1992 | Stokbroekx et al. | 514/252 |

FOREIGN PATENT DOCUMENTS 58-77866 5/1983 Japan .................. 544/238

OTHER PUBLICATIONS

Steiner et al. Jour Med Chem vol 24 pp. 59-63 (1981).
Bellasio et al Il Farmaco vol. 24 pp. 919-929 (1969).

Primary Examiner—Donald G. Daus
Attorney, Agent, or Firm—Charles J. Metz

[57] ABSTRACT

Anti-virally active pyridazinamines, compositions containing the same and methods of treating viral diseases in warm-blooded animals.

8 Claims, No Drawings

ANTI-VIRALLY ACTIVE PYRIDAZINAMINES

CROSS-REFERENCE TO RELATED APPLICATIONS

This application is a division of copending application Ser. No. 637,091, filed Jan. 3, 1991, now U.S. Pat. No. 5,157,035, which was a division of application Ser. No. 702,772, filed Feb. 15, 1985, now U.S. Pat. No. 5,001,125, which was a continuation-in-part of application Ser. No. 593,444, filed Mar. 26, 1984, now abandoned.

BACKGROUND OF THE INVENTION

The present invention is concerned with anti-viral agents, pharmaceutical compositions containing these agents and methods of treating warm-blooded animals suffering from viral diseases.

Viral infections are generally taught to be responsible for a number of diseases of various nature such as, for example, rabies, hepatitis, herpes, common cold etc. . . . More particularly the latter disease is widely spread throughout the world and is a major cause of sickness and absence from work. An agent capable of treating said disease would be a great benefit to mankind and certainly be of great economic importance.

Up until now no such agents are available and there exists no established chemotherapeutic agent against the said disease.

The present invention discloses the useful anti-viral properties of a number of pyridazine derivatives and their use in the treatment of viral diseases. Some of the pyridazinamines of the present invention are known in the art as intermediates for the synthesis of other useful compounds or as compounds having certain pharmacological Properties. These compounds and a number of structurally closely related compounds can be found in the following references.

In J. Med. Chem. 24, 59–63 (1981) there are described a number of 1H-imidazolyl-pyridazines, while in European Patent Number 55,583, U.S. Pat. Nos. 4,110,450, 4,104,385 and 2,985,657 a number of piperazinyl, pyrrolidinyl and piperidinyl substituted pyridazines are described as intermediates. In European Patent Number 9,655 3-chloro-6-[4-(2-methoxyphenyl)-1-piperazinyl]-Pyridazine and 1-chloro-4-(4-hydroxypiperidino)phtalazine are also described as intermediates. Moreover a number of substituted 1-piperazinyl-pyridazines are described in J. Med. Chem. 6, 541–4 (1963). in ibid. 8, 104–107 (1965) and ibid. 15, 295–301 (1972) as compounds having adrenolytic, anti-histaminic or analgesic activity.

The compounds of the present invention differ from the cited prior-art compounds by the specific substitution on the pyridazine moiety and particularly by their useful anti-viral properties.

DESCRIPTION OF THE PREFERRED EMBODIMENTS

According to the present invention, there are provided anti-virally active pyridazinamines which may structurally be represented by the formula

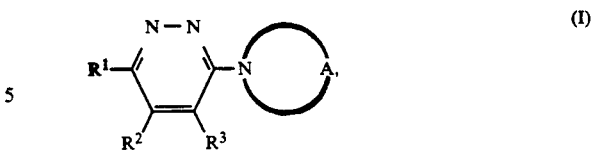

the pharmaceutically acceptable acid-addition salts and/or possible stereochemically isomeric forms and/or possible tautomeric forms thereof, wherein $R^1$ is a member selected from the group consisting of hydrogen, halo, 1H-imidazol-1-yl, lower alkyloxy, aryloxy, aryllower alkyloxy lower alkylthio, arylthio, hydroxy, mercapto, amino, lower alkylsulfinyl, lower alkylsulfonyl, cyano, lower alkyloxycarbonyl, lower alkylcarbonyl, and lower alkyl;

$R^2$ and $R^3$ are, each independently, members selected from the group consisting of hydrogen and lower alkyl, or $R^2$ and $R^3$ combined may form a bivalent radical of formula —CH=CH—CH=CH—;

A is a bivalent radical of formula:

 (a)

 (b)

 (c)

or

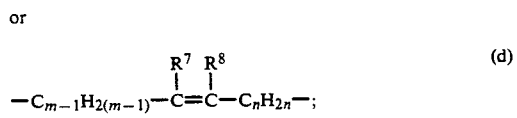 (d)

wherein one of the hydrogen atoms within the radical $C_mH_{2m}$, $C_{m-1}H_{2(m-1)}$ or $C_nH_{2n}$ may be replaced by lower alkyl or aryl;

m and n are, each independently, integers of from 1 to 4 inclusive, the sum of m and n being 3, 4 or 5;

$R^4$ is a member selected from the group consisting of hydrogen; lower alkyl; aryl; thiazolyl; pyrimidinyl; quinolinyl; lower alkylcarbonyl; lower alkyloxycarbonyl; aryllower alkyl; diaryllower alkyl; phenyl being substituted with arylcarbonyl; pyridinyl, being optionally substituted with cyano or lower alkyl; cyclohexyl and cyclohexenyl both being optionally substituted with up to two substituents independently selected from the group consisting of cyano and aryl:

$R^5$ is hydrogen; lower alkyl; aryl; hydroxy; lower alkyloxy: aryloxy: lower alkyloxy being substituted with morpholine, pyrrolidine or piperidine; amino; (lower alkyloxycarbonyl)amino; arylamino; (aryl)(-lower alkyl)amino; (aryllower alkyl)amino; (aryllower alkenyl)amino; (aryllower alkenyl)(lower alkyl)amino; arylcarbonyloxy;

$R^6$ is hydrogen; aryl; lower alkyl: (lower alkylcarbonyl amino)lower alkyl, aryllower alkyl; arylcarbonyllower alkyl; aminocarbonyl; arylcarbonyl; arylaminocarbonyl; (aryllower alkyl)carbonyl, lower alkyloxycarbonyl; indolyl; pyridinyl;

$R^7$ and $R^8$ are, each independently, members selected from the group consisting of hydrogen, lower alkyl, aryl, aryllower alkyl and pyridinyl;

wherein aryl is phenyl, being optionally substituted with up to 3 substituents, each independently selected from the group consisting of halo lower alkyl, trifluoromethyl, nitro, amino, lower alkyloxy hydroxy and lower alkyloxycarbonyl; thienyl; and naphthalenyl.

As used in the foregoing definitions the term halo is generic to fluoro, chloro, bromo and iodo; "lower alkyl" is meant to include straight and branched saturated hydrocarbon radicals, having from 1 to 6 carbon atoms, such as, for example, methyl, ethyl, 1-methylethyl. 1,1-dimethylethyl, propyl, butyl pentyl, hexyl and the like; "lower alkenyl" refers to alkenyl radicals having from 2 to about 6 carbon atoms, such as, for example, 2-propenyl, 2-butenyl, 3-butenyl, 2-pentenyl and the like.

The compounds of formula (I) can generally be prepared by N-alkylating an amine of formula (II) with a reagent of formula (III) following art-known N-alkylating procedures.

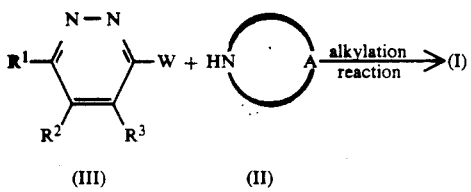

In (III) W represents an appropriate reactive leaving group such as, for example, halo, i.e. fluoro, chloro, bromo or iodo, or a sulfonyloxy group, e.g. methylsulfonyloxy or 4-methylphenylsulfonyloxy, a lower alkyloxy or lower alkylthio group.

The alkylation reactions can conveniently be conducted in an inert organic solvent such as, for example, an aromatic hydrocarbon, e.g. benzene, methylbenzene, dimethylbenzene, and the like; a lower alkanol, e.g., methanol, ethanol, 1-butanol and the like: a ketone, e.g., 2-propanone, 4-methyl-2-pentanone and the like; an ether, e.g., 1,4-dioxane, 1,1'-oxybisethane, tetrahydrofuran and the like; a dipolar aprotic solvent such as, for example, N,N-dimethylformamide (DMF); N,N-dimethylacetamide (DMA); dimethyl sulfoxide (DMSO); nitrobenzene; 1-methyl-2-pyrrolidinone; and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. In some circumstances the addition of an iodide salt, preferably an alkali metal iodide, is appropriate. The alkylation reactions can also be conducted by mixing and/or melting the reactants together, optionally in the presence of the bases mentioned hereinabove. Somewhat elevated temperatures may be used to enhance the rate of the reaction.

The compounds of formula (I) can also be converted into each other by an appropriate functional groupstransformation reaction. For example, the compounds of formula (I), wherein A is a radical of formula (b) wherein $R^4$ is a hydrogen radical said compounds being represented by the formula (I-a) may be alkylated or acylated with a reagent of formula (IV) following the procedures described hereinabove for the preparation of (I) starting from (II) and (III) thus obtaining a compound of formula (I-b).

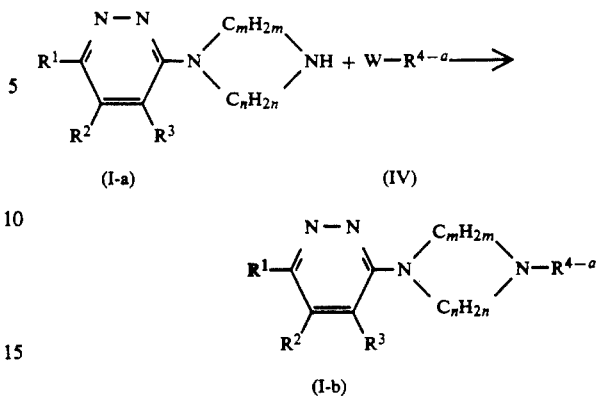

In (IV). W has the previously defined meaning, and $R^{4-a}$ is as $R^4$, provided that it is not hydrogen.

The compounds of formula (I), wherein A is a radical of formula (b), wherein $R^4$ is lower alkyl, aryllower alkyl, diaryllower alkyl, cyclohexyl or cyclohexenyl, said $R^4$ being represented by $R^{4-b}$ and said compounds by the formula (I-c). may be prepared by reductively N-alkylating a compound of formula (I-a) with an appropriate carbonyl-compound of formula $(R^{4-b-1})=C=O$, said $(R^{4-b-1})=C=O$ being a compound of formula $R^{4-b}$—H, wherein a —$CH_2$-radical is oxidated to a carbonyl radical.

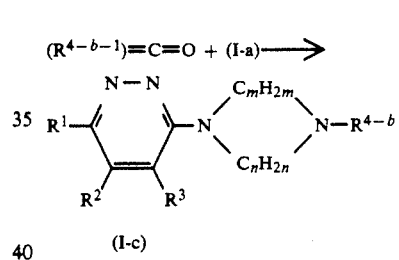

Said reductive N-alkylation reaction may conveniently be carried out by catalytically hydrogenating a stirred and heated mixture of the reactants in a suitable reaction-inert organic solvent according to art-known catalytic hydrogenating procedures. The reaction mixture may be stirred and/or heated in order to enhance the reaction rate. Suitable solvents are, for example, water; lower alkanols, e.g. methanol, ethanol, 2-propanol and the like; cyclic ethers, e.g. 1,4-dioxane and the like; halogenated hydrocarbons, e.g. trichloromethane and the like; N,N-dimethylformamide; dimethyl sulfoxide and the like; or a mixture of 2 or more of such solvents. The term "art-known catalytic hydrogenating procedures" means that the reaction is carried out under hydrogen atmosphere and in the presence of an appropriate catalyst such as for example, palladium-on-charcoal, platinum-on-charcoal and the like. In order to prevent the undesired further hydrogenation of certain functional groups in the reactants and the reaction products it may be advantageous to add an appropriate catalyst-poison to the reaction mixture e.g., thiophene and the like.

The compounds of formula (I), wherein A is a radical of formula (b), wherein $R^4$ is hydrogen can be converted into the corresponding compounds wherein $R^4$ is an optionally substituted 2-cyclohexenyl radical, by reacting the former compounds with an appropriate cyclohexanone derivative in the presence of a suitable solvent such as, for example a hydrocarbon, e.g. benzene, methylbenzene and the like. In some cases it may be advantageous to supplement the reaction mixture with an appropriate acid, e.g. 4-methylsulfonic acid and the like.

Or, conversely, the compounds of formula (I), wherein A is a radical of formula (b) wherein $R^4$ is lower alkyloxycarbonyl or lower alkylcarbonyl may be deacylated following art-known procedures, e.g. by reacting the starting compounds with an appropriate acidic or basic solution.

Similarly, the compounds of formula (I) wherein A is a radical of formula (c) wherein $R^5$ is (lower alkyloxycarbonyl)amino may be converted into the corresponding amino-compounds.

The compounds of formula (1) wherein A is a radical of formula (c) wherein $R^5$ is hydroxy can be converted into the corresponding compounds of formula (I) wherein A is a radical of formula (d) by an elimination reaction. This can be accomplished by reacting the former compounds with a suitable acidic solution preferably at higher temperatures. Suitable acidic solutions contain one or more acids such as sulfuric, hydrochloric, acetic and the like acids in admixture with water and/or an organic solvent such as methanol, ethanol and the like.

Or the starting hydroxy containing compounds can be reacted with an appropriate deshydratating agent such as, for example, phosphoryl chloride, thionyl chloride, phosphor trichloride, preferably in the presence of a suitable solvent such as, for example, pyridine, N,N-dimethylformamide (DMF) and the like.

The compounds of formula (I) containing a cyclohexenyl radical may be converted into the corresponding cyclohexyl containing compounds by an appropriate reduction procedure e.g. by reacting the former compounds with a metal hydride e.g. sodium borohydride, in a suitable solvent, e.g. an alkanol such as methanol and the like, optionally in the presence of a base, e.g. sodium methoxide and the like.

The compounds of formula (I), wherein $R^1$ is halo may be converted into the corresponding compounds wherein $R^1$ is lower alkyloxy, aryloxy, aryllower alkyloxy, lower alkylthio or arylthio by reacting the said halo containing compounds with an appropriate aromatic or aliphatic alcohol or mercaptane. The said reaction may be conducted in an appropriate solvent such as, for example a ketone, e.g. 2-propanone, DMF, DMA and the like solvents. The addition of a suitable base such as, for example, an alkali metal hydride, e.g. sodium hydride, an alkali metal carbonate, e.g. sodium carbonate may be used to enhance the rate of the reaction. Alternatively, the starting halo compounds may be reacted with an appropriate alkali metal alkoxide, aryloxide or (aryl substituted)alkoxide in a suitable solvent, preferably in the corresponding alcohol, thus preparing the desired compounds of formula (I) wherein $R^1$ is lower alkyloxy, aryloxy and aryllower alkyloxy.

The compounds of formula (I) wherein $R^1$ is arylmethyloxy may be converted into the corresponding hydroxy compounds following art-known procedures for the removal of the arylmethyl group, e.g. by reacting the starting compounds with an acidic solution or with hydrogen in the presence of an appropriate catalyst in a suitable solvent.

The compounds of formula (I), wherein $R^1$ is halo may be converted into the corresponding compounds wherein $R^1$ is hydrogen, following art-known hydrogenolysis procedures, i.e. by heating the starting compounds in a suitable solvent under hydrogen atmosphere in the presence of an appropriate catalyst, e.g. palladium-on-charcoal and the like catalysts.

The compounds of formula (I), wherein $R^1$ is halo may further be converted into the corresponding mercapto containing compounds by reacting the former compounds with hydrogen sulfide or a reagent capable of generating hydrogen sulfide, e.g. thiourea in the presence of a base.

The compounds of formula (I) wherein $R^1$ is lower alkyloxycarbonyl may be converted into the corresponding lower alkylcarbonyl compounds by reacting the starting compounds with an appropriate ester in the presence of an alkali metal in a suitable alcohol.

The compounds of formula (I) have basic properties and, consequently, they may be converted to their therapeutically active non-toxic acid-addition salt forms by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

A number of intermediates and starting materials in the foregoing preparations are known compounds which may be prepared according to art-known methodologies as described, for example, in U.S. Pat. Nos. 2,997,472: 2,979,507: 2,997,474 and 3,002,976.

The intermediates of formula (II), wherein A is a radical of formula (b), wherein $R^4$ is other than hydrogen, said $R^4$ being represented by $R^{4-a}$ and said intermediates by the formula (II-a). may be prepared by alkylating an amine of formula (V) with a reagent of formula (IV). thus yielding an intermediate of formula (VI), and subsequently eliminating the group P. In (V) and (VI) P is an appropriate protective group such as, for example, lower alkyloxycarbonyl, arylmethoxycarbonyl, arylmethyl, arylsulfonyl and the like. The elimination of P in (VI) may generally be carried out following art-known Procedures such as, for example, by hydrolysis in alkaline or acidic medium.

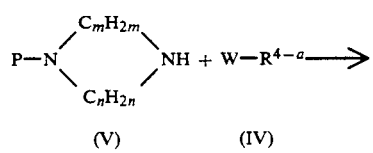

(V)     (IV)

-continued

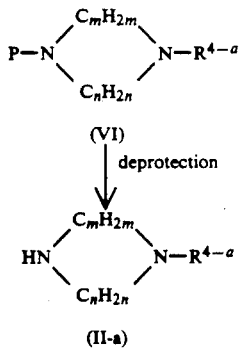

The intermediates of formula (VI) may also be prepared by N-alkylating an amine of formula (VII) with a reagent of formula (VIII), following art-known N-alkylating procedures.

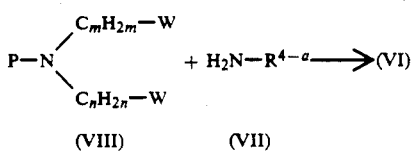

The reaction of (IV) with (V) and of (VII) with (VIII) may be conducted following the same procedures described hereinabove for the preparation of (I) starting from (II) and (III).

The intermediates of formula (II), wherein A is a radical of formula (c), wherein $R^6$ is hydrogen and $R^5$ is a radical of formula $-NR^9R^{10}$, said $-NR^9R^{10}$ being arylamino, (aryl)(lower alkyl)-amino, (aryllower alkyl)amino, (aryllower alkenyl)(lower alkyl)amino, (aryllower alkenyl)amino, said intermediates being represented by the formula (II-b), can conveniently be prepared by reductively N-alkylating a ketone of formula (IX) with an amine of formula (X), thus yielding an intermediate of formula (XI), and subsequently eliminating the protective group P. In (IX) and (XI), P has the previously described meaning.

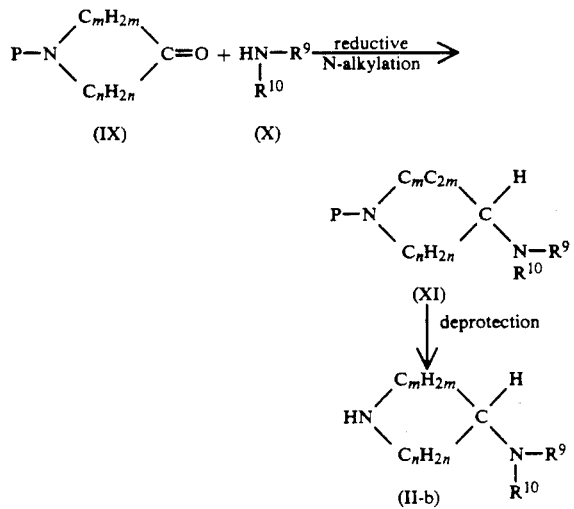

The said reductive amination may conveniently be carried out by catalytically hydrogenating a mixture of the reactants in a suitable reaction-inert medium, according to art-known procedures.

The intermediates of formula (II), wherein A is a bivalent radical of formula (c) wherein $R^5$ is hydroxy and $R^6$ is aryl, lower alkyl or substituted lower alkyl can be prepared by reacting (IX) with an appropriate Grignard reagent in a suitable solvent. The thus obtained hydroxy containing intermediates may be deprotected or further reacted with a suitable acidic solution in order to eliminate a water molecule and subsequently be deprotected thus preparing intermediates of formula (II) wherein A is a radical of formula (d).

The compounds of formula (I) show anti-viral activity and are particularly attractive due to their favourable therapeutic index, resulting from an acceptable low degree of cell toxicity, combined with a desirable anti-viral activity at low doses.

The useful anti-viral properties of the compounds of formula (I) are demonstrated in the following test procedure.

Rhinovirus Cythopatic Effect Test

Rhinovirus sensitive Hela cells were seeded into Minemal Essential Medium (MEM) supplemented with 5% inactivated foetal calf serum and non essential amino acids. The seeded cells were incubated overnight at 37° C. in a 5% $CO_2$ atmosphere. After 24 hours the cells were treated with solutions of the test compounds in a solvent containing 1 part by volume of DMSO and 7 parts by volume of MEM supplemented with 10% inactivated calf serum, or with the said solvent.

Both the solvent and drug treated cells were incubated for 3 hours at 37° C. and subsequently a standardized inoculum of human rhinovirus was added. During a further incubation period at 33° C., the rhinovirus was allowed to grow in the Hela cells. Scoring of the results was delayed until a complete (100%) cytopathic effect was obtained in the virus controls (cells treated with solvent and virus).

Anti-viral activity was scored as the lowest concentration of the tested drug in µg/ml inhibiting at least 75% of the cytopathic effect observed in the virus controls.

Additionally, some of the compounds of the present invention show also analgetic and antitussive properties which properties can be demonstrated, for example by the Tail Withdrawal Reflex test and the Writhing Test described in Arzneim. Forsch., 25, 1505–1509 (1975) and in Arzneim. Forsch., 15, 107–117 (1965).

In view of their useful pharmacological properties, the compounds of formula (I) and their acid-addition salts are very useful in the treatment of viral diseases.

In order to enhance the ease of administration, the subject compounds may be formulated into various pharmaceutical forms. To prepare the pharmaceutical compositions of this invention, an effective amount of the particular compound, in base or acid-addition salt form, as the active ingredient is combined in intimate admixture with a pharmaceutically acceptable carrier, which carrier may take a wide variety of forms depending on the form of preparation desired for administration.

These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed.

In the compositions suitable for percutaneous administration, the carrier optionally comprises a penetration enhancing agent and/or a suitable wettable agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In a further aspect of the present invention there is provided a method of treating viral diseases in warm-blooded animals suffering from said viral diseases, which method comprises the systemic administration to warm-blooded animals of an anti-virally effective amount of a compound of formula (I). a pharmaceutically acceptable acid addition salt, a possible stereoisomeric or tautomeric form thereof. Suitable doses administered daily to subjects are varying from 0.01 mg to 1 g, preferably from 1 mg to 500 mg.

Preferred methods of treating viral diseases in warm-blooded animals suffering from said viral diseases, are those methods comprising the systemic administration to warm-blooded animals of an anti-virally effective amount of a compound having the formula

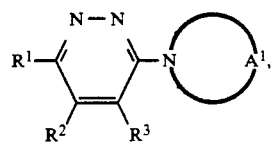
(I')

a pharmaceutically acceptable acid-addition salt and/or a possible stereoisomeric and/or a tautomeric form thereof, wherein $R^1$, $R^2$ and $R^3$ have the previously defined meaning and $A^1$ is a bivalent radical having the formula (a), (b), (c) or (d);

provided that i) when $R^1$, $R^2$ and $R^3$ are hydrogen radicals and $A^1$ is a radical of formula (b), then $R^4$ is other than 3,3-diphenylpropyl;

ii) when $R^1$ is hydrogen and $R^2$ and $R^3$ combined form a bivalent CH=CH—CH=CH radical, then

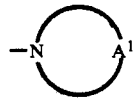

is other than piperidinyl;

iii) when $R^1$ halo, $R^2$ is lower alkyl and $R^3$ is hydrogen, then

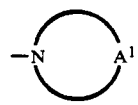

is other than piperidinyl and hexahydro-1H-azepinyl.

iv) when $R^1$ is chloro, and $A^1$ is a bivalent radical of formula (b) then $R^4$ is other then (dimethoxyphenyl)-methyl, (dimethoxyphenyl)ethyl, α-methyl-phenethyl or (2-methylphenyl)methyl.

Preferred compositions within the invention are those comprising an inert carrier and an anti-virally effective amount of a compound of formula (I'). a pharmaceutically acceptable acid-addition salt and/or a possible stereochemically isomeric form and/or a tautomeric form thereof.

An additional feature of the present invention consists in the fact that some of the compounds of formula (I) and/or the pharmaceutically acceptable acid-addition salts and/or possible stereochemically isomeric and/or the possible tautomeric forms thereof are which compounds are represented by the formula

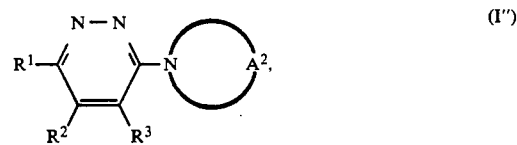
(I'')

wherein $R^1$, $R^2$ and $R^3$ have the previously described meaning and $A^2$ is a bivalent radical having the formula (a), (c), (d) or

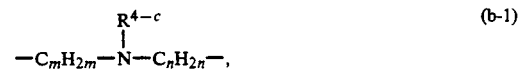
(b-1)

wherein m and n have the previously described meaning and one of the hydrogen atoms within the radical $C_mH_{2m}$, $C_{m-1}H_{(2m-1)}$ or $C_nH_{2n}$ may be replaced by lower alkyl or aryl; and $R^{4-c}$ is a member selected from the group consisting of aryl: thiazolyl; pyrimidinyl; quinolinyl: lower alkylcarbonyl, lower alkyloxycarbonyl; diaryllower alkyl; phenyl being substituted with arylcarbonyl: pyridinyl, being optionally substituted with cyano or lower alkyl; cyclohexyl and cyclohexenyl both being optionally substituted with up to two substituents independently selected from the group consisting of cyano and aryl: provided that i) when $A^2$ is a radical of formula (c) and $R^6$ is hydrogen, then $R^5$ is other than hydrogen, hydroxy or lower alkyl;

ii) when $R^1$, $R^2$ and $R^3$ are hydrogen radicals and $A^2$ is a radical of formula (b-1), then $R^{4-c}$ is other than 3,3-diphenylpropyl;

iii) when $R^2$ and $R^3$ are hydrogen radicals and $A^2$ is a radical of formula (a), then $R^1$ is other than halo:

iv) when $R^1$ is chloro, $R^2$ and $R^3$ are hydrogen radicals and $A^2$ is a radical of formula (b-2), then $R^{4-c}$ is other than 2-methoxyphenyl.

v) When $R^1$ is chloro, and $A^2$ is a bivalent radical of formula (b) then $R^{4-c}$ is other then (dimethoxyphenyl)methyl, (dimethoxyphenyl)ethyl, α-methyl-phenethyl or (2-methylphenyl)methyl.

Particularly preferred methods of treating viral diseases in warm-blooded animals suffering from same, are those methods comprising the systemic administration to warm-blooded animals of an anti-virally effective amount of a compound having the formula (I'') a pharmaceutically acceptable acid-addition salt and/or a possible stereochemically isomeric form and/or a possible tautomeric form thereof.

Particularly preferred compositions within the invention are those comprising an inert carrier and an anti-virally effective amount of a compound of formula (I''), a pharmaceutically acceptable acid-addition salt and/or a possible stereochemically isomeric form and/or a possible tautomeric form thereof.

Within the group of the said new compounds, those compounds of formula (I'') are preferred wherein $A^2$ is a bivalent radical of formula (b), wherein $R^{4-c}$ is aryl, pyridinyl, pyrimidinyl, lower alkyloxycarbonyl, aryllower alkyl, diaryllower alkyl, quinolinyl, or wherein $A^2$ is a bivalent radical of formula (c), wherein $R^5$ is hydrogen, aryl, arylamino, (aryl)(lower alkyl)amino, hydroxy, indolyl and $R^6$ is hydrogen, aryl, arylcarbonyl, (arylcarbonyl)lower alkyl, or wherein $A^2$ is a bivalent radical of formula (d).

Particularly preferred new compounds are those wherein the bivalent radical $A^2$ is as defined for the preferred new compounds and wherein $R^2$ and $R^3$ are both hydrogen radicals.

More particularly preferred new compounds are those wherein $R^2$, $R^3$ and $A^2$ are as defined for the particularly preferred compounds and wherein in the said bivalent radical $A^2$ having the formula (b) m is the integer 2 or 3 and n is 2, in the radical $A^2$ having the formula (c) m is the integer 1 or 2 and n is the integer 2, and in the radical $A^2$ of formula (d), m is the integer 1 or 2 and n is the integer 2.

Especially preferred new compounds are those wherein $R^2$, $R^3$, $A^2$, m and n are as defined for the previously mentioned more particularly preferred new compounds and wherein $R^1$ is halo, lower alkyloxy, aryloxy, lower alkylthio, arylthio and cyano.

More especially preferred new compounds are those wherein $R^2$, $R^3$, $A^2$, m and n are as defined for the previously mentioned more particularly preferred new compounds, and wherein $R^1$ is halo.

The most preferred compounds within the invention are selected from the group consisting of 3-bromo-6-[4-(3-methylphenyl)-1-piperazinyl]pyridazine, 3-chloro-6-[3,6-dihydro-4-(3-methylphenyl)-1(2H)-pyridinyl]-pyridazine and the pharmaceutically acceptable acid-addition salts thereof.

Some of the compounds of this invention may have several asymmetric centra in their structure. Pure stereoisomeric forms of the compounds of formula (I) may be obtained by art-known separation procedures. For example, diastereomers may be separated by selective crystallization or by application of chromatographic techniques, while enantiomers may be separated by the selective crystallization of their diastereomeric salts with optically active acids. Pure stereoisomeric forms may also be obtained by stereospecific syntheses starting from the corresponding stereoisomerically pure forms of the appropriate starting materials. Stereochemically isomeric forms of the compounds of formula (I) are intended to be embraced within the scope of this invention.

The following examples are intended to illustrate and not to limit the scope of the present invention in all its aspects. Unless otherwise stated all parts therein are by weight.

EXAMPLES

A. Preparation of Intermediates

Example 1

A mixture of 221 parts of 4-fluorobenzeneacetonitrile, 700 parts of sodium methoxide solution 30% and 900 parts of dimethylbenzene was stirred for 5 minutes. Then there were added dropwise 309 parts of methyl 2-propenoate (exothermic reaction: temperature rose to 65° C.). Upon completion, stirring was continued overnight at reflux temperature. The methanol was distilled off till an internal temperature of 110° C. was reached. After cooling, 1000 parts of a hydrochloric acid solution 6N were added dropwise and the whole was stirred and refluxed for 5 minutes. Upon cooling, the layers were separated. The organic phase was dried, filtered and evaporated. The residue was stirred and refluxed for 4 hours together with 500 parts of acetic acid, 500 parts of water and 500 parts of a hydrochloric acid solution. After cooling, the product was extracted with trichloromethane. The extract was washed successively with water, with a diluted sodium hydroxide solution and again with water till neutralization, dried, filtered and evaporated. The residue was crystallized from 2-propanol, yielding 134.5 parts of 1-(4-fluorophenyl)-4-oxocyclohexanecarbonitrile; mp. 91.8° C. (intermediate 1).

Example 2

A mixture of 17.6 parts of 1-(phenylmethyl)piperazine, 8.4 parts of ethyl 4-fluorobenzoate and 45 parts of N,N-dimethylacetamide was stirred and refluxed for 22 hours. The reaction mixture was cooled and poured onto 500 parts of water. The product was extracted three times with benzene. The combined extracts were washed three times with a lot of water, dried, filtered and evaporated. The residue was stirred in hexane. The product was filtered off, washed with hexane and dried in vacuo, yielding 12.5 parts (77%) of ethyl 4-[4-(phenylmethyl)-1-piperazinyl]benzoate (intermediate 2).

Example 3

A mixture of 14 parts of ethyl 4-(methylamino)-1-piperidinecarboxylate, 13 parts of (3-chloro-1- propenyl)benzene, 26.5 parts of sodium carbonate and 240 parts of 4-methyl-2-pentanone was stirred and refluxed over week-end using a water separator. The reaction mixture was cooled, water was added and the layers were separated. The organic phase was dried, filtered and evaporated. The residue was converted into the ethanedioate salt in 2-propanol and 2-propanone. The salt was filtered off and dried, yielding 23.4 parts of (E)-ethyl 4-[methyl(3-phenyl-2-propenyl)amino]-1-piperidinecarboxylate ethanedioate (1:1); mp. 160.2° C. (intermediate 3).

Example 4

To a stirred mixture of 19 parts of 1-(phenylmethyl)-4-piperidinol, 15.2 parts of N,N-diethylethanamine and 180 parts of methylbenzene were added dropwise (slowly) 14 parts of benzoyl chloride. Upon completion, stirring was continued for 3 hours at room temperature. The formed hydrochloride salt of benzoyl chloride was filtered off and washed with methylbenzene. The filtrate was evaporated. The oily residue was purified by column chromatography over silica gel using a mixture of trichloromethane and methanol (95:5 by volume) as eluent. The pure fractions were collected and the eluent was evaporated. The residue was converted into the hydrochloride salt in 2-propanol. The salt was filtered off and dried, yielding 18 parts (54%) of [1-(phenylmethyl)-4-piperidinyl] benzoate hydrochloride; mp. 225.9° C. (intermediate 4).

Example 5

To a stirred mixture of 7.8 parts of sodium amide 5% in benzene and 135 parts of methylbenzene was added dropwise a solution of 11.7 parts of benzeneacetonitrile in 45 parts of methylbenzene at 25° C (cooling was necessary). After stirring for 30 minutes at 30° C., there was added dropwise a solution of 24.7 parts of ethyl 1-(phenylmethyl)-4-piperidinecarboxylate in 45 parts of methylbenzene at 30° C. Upon completion, stirring was continued overnight at 80° C. The reaction mixture was cooled, 12 parts of ethanol were added and the whole was poured into ice water. The layers were separated and the aqueous phase was neutralized with acetic acid The oily Product was extracted with trichloromethane. The extract was dried, filtered and evaporated. The residue was crystallized from 4-methyl-2-pentanone, yielding 12 parts (38%) of α-[hydroxy[1-(phenylmethyl)-4-piperidinyl]methylidene]-benzeneacetonitrile: mp. 191.9° C. (intermediate 5).

To 200 parts of water were added carefully 200 parts of acetic acid while stirring and cooling. Then there were added dropwise (slowly) 368 parts of sulfuric acid. 90 Parts of α-[hydroxy[1-(phenylmethyl)-4-piperidinyl]methylidene]benzeneacetonitrile were added and the whole was stirred and refluxed overnight. The acetic acid was evaporated and the residue was poured into crushed ice. The mixture was alkalized with concentrate ammonium hydroxide and the oily product was extracted with trichloromethane. The extract was dried, filtered and evaporated, yielding 79 parts (96.3%) of 2-phenyl-1-[1-(phenylmethyl)-4-piperidinyl]ethanone as a residue (intermediate 6).

Example 6

A mixture of 93 parts of N-(2-chloroethyl)-N-(3-chloropropyl)-4-methylbenzenesulfonamide, 30.3 parts of 2,3-dimethylbenzenamine, 63.6 parts of sodium carbonate, 1 part of potassium iodide and 240 parts of cyclohexanol was stirred and refluxed over weekend using a water separator. After cooling, the reaction mixture was poured into water. The product was extracted with methylbenzene. The extract was washed twice with water, dried, filtered and evaporated. The residue was crystallized from 2-propanol and a small amount of tetrahydrofuran. The product was filtered off and dried, yielding 47.8 parts (53.3%) of 1-(2.3-dimethylphenyl)-hexahydro-4-[(4-methylphenyl)sulfonyl]-1H-1.4-diazepine; mp. 86.2° C. (intermediate 7).

In a similar manner there were also prepared: 1-[2-methoxy-5-(trifluoromethyl)phenyl]piperazine hydrochloride; mp. 226.8° C. (intermediate 8);

1-[(4-methylphenyl)sulfonyl]-4-(2,4,6-trimethylphenyl)piperazine (intermediate 9);

1-(3,5-dichlorophenyl)hexahydro-4-[(4-methylphenyl)sulfonyl]-1H-1,4-diazepine (intermediate 10);

1-(3-chlorophenyl)hexahydro-4-[(4-methylphenyl)-sulfonyl)-1H-1,4-diazepine; mp. 116.6° C. (intermediate 11);

hexahydro-1-(2-methoxyphenyl)-4-[(4-methylphenyl)sulfonyl]-1H-1,4-diazepine as a residue (intermediate 12); and hexahydro-1-[(4-methylphenyl)sulfonyl]-4-[3-(trifluoromethyl)phenyl]-1H-1,4-diazepine as a residue (intermediate 13).

Example 7

To a stirred mixture of 180 parts of 1-[(4-methylphenyl)sulfonyl]-4-(2,4,6-trimethylphenyl)piperazine and 450 parts of water were added dropwise 675 parts of sulfuric acid. The whole was stirred and refluxed for 4 hours. After cooling, the whole was treated with an ammonium hydroxide solution. The product was extracted with dichloromethane. The extract was dried, filtered and evaporated, yielding 70 parts (69%) of 1-(2,4,6-trimethylphenyl)piperazine as a residue (intermediate 14).

In a similar manner there were also prepared:

4-(3-methylphenyl)-4-piperidinecarboxamide (intermediate 15):

1-(2,3-dimethylphenyl)hexahydro-1H-1,4-diazepine as a residue (intermediate 16);

hexahydro-1-(2-methoxyphenyl)-1H-1,4-diazepine monohydrochloride; mp 176.6° C. (intermediate 17); and hexahydro-1-[3-(trifluoromethyl)phenyl]-1H-1,4-diazepine monohydrochloride; mp. 191.1° C. (intermediate 18).

Example 8

A mixture of 7.9 parts of ethyl 3-oxo-1-pyrrolidinecarboxylate, 5.35 parts of 3-methylbenzenamine, 1 part of a solution of thiophene in methanol 4% and 200 parts of methanol was hydrogenated at normal pressure and at 50° C. with 2 parts of palladium-on-charcoal catalyst 10%. After the calculated amount of hydrogen was taken up, the catalyst was filtered off and the filtrate was evaporated, yielding 12.4 parts (100%) of ethyl 3-[(3-methylphenyl)amino]-1-pyrrolidinecarboxylate as a residue (intermediate 19).

In a similar manner there were also prepared:
N-(2.3-dimethylphenyl)-1-(phenylmethyl)-3-piperidinamine ethanedioate(1:1); mp. 151.6° C. (intermediate 20):

N-phenyl-1-(phenylmethyl)-3-piperidinamine as a residue (intermediate 21);

ethyl 3-[(2,3-dimethylphenyl)amino]-1-pyrrolidinecarboxylate as a residue (intermediate 22);

ethyl 4-[[3-(trifluoromethyl)phenyl]amino]-1-piperidinecarboxylate monohydrochloride (intermediate 23);

N-(3-methylphenyl)-1-(phenylmethyl)-3-piperidinamine as a residue (intermediate 24); and ethyl 3-[[3-(trifluoromethyl)phenyl]amino]-1-pyrrolidinecarboxylate as a residue (intermediate 25).

Example 9

To a stirred solution of 152 parts of 3-methyl-1-(phenylmethyl)-4-piperidinone in 900 parts of methylbenzene were added dropwise 218 parts of ethyl carbonochloridate at room temperature. Upon completion, stirring was continued overnight at reflux. After cooling, the reaction mixture was washed with water and hydrochloric acid, dried, filtered and evaporated. The residue was distilled, yielding 120.5 parts (83%) of ethyl 3-methyl-4-oxo-1-piperidinecarboxylate; bp. 98°-105° C. at 1 mm pressure (intermediate 26).

Example 10

To a stirred and refluxed Grignard complex previously prepared starting from a mixture of 4.2 parts of 1-bromo-3-chlorobenzene, 5.4 parts of magnesium and 135 parts of tetrahydrofuran were added dropwise 19 parts of 1-(phenylmethyl)-3-piperidinone. Upon completion, stirring was continued for 1 hour at reflux temperature. After cooling, the reaction mixture was poured into ice water and 12.5 parts of acetic acid. The layers were separated. The aqueous phase was extracted with trichloromethane. The organic layer was washed with water, dried, filtered and evaporated. The residue was converted into the hydrochloride salt in 2-propanol. The salt was filtered off and dried, yielding 26 parts (76%) of 3-(3-chlorophenyl)-1-(phenylmethyl)-3-piperidinol hydrochloride (intermediate 27).

In a similar manner there were also prepared:

ethyl 4-hydroxy-4-(2-thienyl)-1-piperidinecarboxylate: mp. 146.2° C.: (intermediate 28);

ethyl 4-hydroxy-4-(1-naphthalenyl)-1-piperidinecarboxylate; mp. 109.2°-114.8° C.; (intermediate 29);

ethyl 3-(4-chloro-3-(trifluoromethyl)phenyl]-3-hydroxy-1-pyrrolidinecarboxylate as a residue; (intermediate 30);

ethyl 4-hydroxy-4-(2-naphthalenyl)-1-piperidinecarboxylate as a residue; (intermediate 31);

3-(3-methylphenyl)-1-(Phenylmethyl)-3-piperidinol hydrochloride (intermediate 32);

cis-3-methyl-4-(3-methylphenyl)-1-(phenylmethyl)-4-piperidinol as a residue (intermediate 33);

ethyl cis-4-(3-fluorophenyl)-4-hydroxy-3-methyl-1-piperidinecarboxylate as a residue (intermediate 34);

ethyl cis-4-hydroxy-3-methyl-4-(2-thienyl)-1-piperidinecarboxylate as a residue (intermediate 35):

ethyl 3-hydroxy-3-(2-thienyl)-1-piperidinecarboxylate (intermediate 36);

3-(3-fluorophenyl)-1-(phenylmethyl)-3-piperidinol hydrochloride (intermediate 37);

ethyl 4-(2,3-dimethylphenyl)-4-hydroxy-1-piperidinecarboxylate (intermediate 38);

3-(2,3-dimethylphenyl)-1-(phenylmethyl)-3-piperidinol hydrochloride (intermediate 39);

3-(3-methylphenyl)-1-(phenylmethyl)-3-pyrrolidinol hydrochloride (intermediate 40);

ethyl 3-[4-chloro-3-(trifluoromethyl)phenyl]-3-hydroxy-1-piperidinecarboxylate as a residue (intermediate 41);

3-(3-fluorophenyl)-1-(phenylmethyl)-3-pyrrolidinol hydrochloride (intermediate 42);

ethyl 4-hydroxy-4-(3-methoxyphenyl)-3-methyl-1-piperidinecarboxylate as a residue (intermediate 43); and 3-(3-methoxyphenyl)-1-(phenylmethyl)-3-pyrrolidinol hydrochloride (intermediate 44).

Example 11

A mixture of 7 parts of 3-(2,3-dimethylphenyl)-1-(phenylmethyl)-3-piperidinol hydrochloride and 200 parts of a hydrochloric acid solution 6N was stirred and refluxed overnight. The reaction mixture was evaporated. Water was added and the base was liberated with ammonium hydroxide. The product was extracted with trichloromethane. The extract was washed with water, dried, filtered and evaporated. The residue was purified by column chromatography over silica gel using a mixture of trichloromethane and ethanol (98:2 by volume) as eluent. The first fraction was collected and the eluent was evaporated, yielding 0.7 parts (12%) of 5-(2,3-dimethylphenyl)-1,2,3,4-tetrahydro-1-(phenylmethyl)pyridine as a residue (intermediate 45).

The second fraction was collected and the eluent was evaporated, yielding 5.3 parts (91%) of 5-(2,3-dimethylphenyl)-1,2,3,6-tetrahydro-1-(phenylmethyl)pyridine as a residue (intermediate 46).

Example 12

A mixture of 8 parts of 3-(3-methylphenyl)-1-(phenylmethyl)-3-pyrrolidinol hydrochloride and 150 parts of a hydrochloric acid solution 6N was stirred and refluxed for 3 hours. After cooling, the reacting mixture was evaporated, yielding 7.4 parts (100%) of 2,3-dihydro-4-(3-methylphenyl)-1-(phenylmethyl)-1H-pyrrole hydrochloride as a residue (intermediate 47).

In a similar manner there were also prepared:

1,2,3,6-tetrahydro-5-(3-methylphenyl)-1-(phenylmethyl)pyridine as a residue (intermediate 48); and 5-(3-fluorophenyl)-1,2,3,6-tetrahydro-1-(phenylmethyl)pyridine hydrochloride (intermediate 49).

Example 13

To a stirred solution of 13 parts of 3-(3-chlorophenyl)-1-(phenylmethyl)-3-piperidinol in 270 parts of methylbenzene were added dropwise 10.9 parts of ethyl carbonochloridate at room temperature. Upon completion, stirring was continued overnight at reflux temperature. After cooling to room temperature, the whole was washed with water and hydrochloric acid. The organic layer Was dried, filtered and evaporated, yielding 7 parts (58%) of ethyl 3-(3-chlorophenyl)-3-hydroxy-1-piperidinecarboxylate as a residue (intermediate 50).

Example 14

A mixture of 11.8 parts of N-(2,3-dimethylphenyl)-1-(phenylmethyl)-3-piperidinamine and 120 parts of methanol was hydrogenated at normal pressure and at room temprature with 2 parts of palladium-on-charcoal catalyst 10%. After the calculated amount of hydrogen was taken up, the catalyst was filtered off over Hyflo and the filtrate was evaporated. The residue was purified by column chromatography over silica gel using a mixture of trichloromethane and methanol (from 99:1 to 95:5 by volume) as eluent. The pure fractions were collected and the eluent was evaporated. The residue was converted into the ethanedioate salt in 2-propanol and 2-propanone. The salt was filtered off and dried, yielding 7 parts (79.5%) of N-(2,3-dimethylphenyl)-3-piperidinamine ethanedioate (1:1): mp. 161.6° C. (intermediate 51).

In a similar manner there were also prepared:

ethyl 4-(1-piperazinyl)benzoate: mp. 102.6° C. (intermediate 52):

(4-piperidinyl) benzoate hydrochloride; mp. 236.8° C. (intermediate 53);

N-phenyl-3-piperidinamine; mp. 79.8° C. (intermediate 54);

N-(3-methylphenyl)-3-piperidinamine as a residue (intermediate 55);

4-[(3-methylphenyl)amino]-4-piperidinecarboxamide as a residue (intermediate 56);

2-phenyl-1-(4-piperidinyl)ethanone hydrochloride: mp. 198.6° C.: (intermediate 57);

3-(3-methylphenyl)piperidine as a residue (intermediate 58);

3-(3-methylphenyl)-3-piperidinol hydrochloride (intermediate 59);

cis-3-methyl-4-(3-methylphenyl)-4-piperidinol as a residue (intermediate 60);

3-(3-fluorophenyl)-3-piperidinol hydrochloride (intermediate 61);

3-(2,3-dimethylphenyl)-3-piperidinol hydrochloride hemihydrate: mp. 135.5° C. (intermediate 62);

3-(2.3-dimethylphenyl)piperidine as a residue (intermediate 63);

3-(3-methylphenyl)-3-pyrrolidinol (intermediate 64);

3-(3-methoxyphenyl)-3-piperidinol hydrochloride as a residue (intermediate 65):

3-(3-fluorophenyl)-3-pyrrolidinol hydrochloride as a residue (intermediate 66); and 3-(3-methoxyphenyl)-3-pyrrolidinol hydrochloride as a residue (intermediate 67).

Example 15

A mixture of 13.10 parts of ethyl 3-[(2,3-dimethylphenyl)amino]-1-pyrrolidinecarboxylate, 28 parts of potassium hydroxide and 240 parts of 2-propanol was stirred and refluxed for 6 hours. The reaction mixture was evaporated. The residue was taken up in water. The product was extracted with dichloromethane. The extract was dried, filtered and evaporated. Yielding 6 parts (63%) of N-(2,3-dimethylphenyl)-3-pyrrolidinamine as a residue (intermediate 68).

In a similar manner there were also prepared:

(E)-N-methyl-N-(3-phenyl-2-propenyl)-4-piperidinamine dihydrochloride hemihydrate: mp. 240.2° C. (intermediate 69);

N-[3-(trifluoromethyl)phenyl]-4-piperidinamine dihydrobromide; mp. 253.2° C. (intermediate 70);

N-(3-methylphenyl)-3-pyrrolidinamine ethanedioate(1:2); mp. 180° C. (intermediate 71);

4-(2-thienyl)-4-piperidinol; mp. 145.9° C. (intermediate 72);

4-(1-naphthalenyl)-4-piperidinol; mp. 185.1°–187.8° C. (intermediate 73);

3-[4-chloro-3-(trifluoromethyl)phenyl]-3-pyrrolidinol; mp. 138.4–142.1° C. (intermediate 74);

4-(2-naphthalenyl)-4-piperidinol (intermediate 75);

N-[3-(trifluoromethyl)phenyl]-3-pyrrolidinamine dihydrochloride (intermediate 76):

cis-4-(3-fluorophenyl)-3-methyl-4-piperidinol as a residue (intermediate 77);

cis-3-methyl-4-(2-thienyl)-4-piperidinol as a residue (intermediate 78);

3-(2-thienyl)-3-piperidinol (intermediate 79);

3-(3-chlorophenyl)-3-piperidinol hydrochloride (intermediate 80):

4-(2.3-dimethylphenyl)-4-piperidinol (intermediate 81);

4-(3-chlorophenyl)-3-methyl-4-piperidinol as a residue (intermediate 82);

3-[4-chloro-3-(trifluoromethyl)phenyl]-3-piperidinol (intermediate 83); and 4-(3-methoxyphenyl)-3-methyl-4-piperidinol as a residue (intermediate 84).

Example 16

A mixture of 3 parts of 3-(3-fluorophenyl)-3-piperidinol hydrochloride and 100 parts of a hydrochloric acid solution 6N was stirred and refluxed for 3 hours. The reaction mixture was evaporated. The residue was taken up in water and ammonium hydroxide. The product was extracted with trichloromethane. The extract was washed with water, dried, filtered and evaporated, yielding 2.2 parts (96%) of 5-(3-fluorophenyl)-1,2,3,6-tetrahydropyridine as a residue (intermediate 85).

Following the same procedure and using equivalent amounts of the appropriate starting materials, there were also prepared:

4-[4-chloro-3-(trifluoromethyl)phenyl]-1,2,3,6-tetrahydropyridine hydrochloride (intermediate 86);

1,2,3,6-tetrahydro-4-(2-thienyl)pyridine hydrochloride (intermediate 87);

1,2,3,6-tetrahydro-4-[3-(trifluoromethyl)phenyl]pyridine as a residue (intermediate 88);

1,2,3,6-tetrahydro-4-(1-naphthalenyl)pyridine hydrochloride; mp. 277.5° C. (intermediate 89):

1,2,3,6-tetrahydro-5-(3-methylphenyl)pyridine hydrochloride (intermediate 90):

3,4-dihydro-3-(2-thienyl)-1H-pyrrole as a residue (intermediate 91); and 3-(2-thienyl)pyrrolidine as a residue (intermediate 92).

Example 17

A mixture of 6.5 parts of 5-(3-fluorophenyl)-1,2,3,6-tetrahydro-1-(phenylmethyl)pyridine hydrochloride and 120 parts of methanol was hydrogenated at normal pressure and at 50° C. with 1 part of palladium-on-charcoal catalyst 10%. After the calculated amount of hydrogen was taken up, the catalyst was filtered off and the filtrate was evaporated, yielding 4.5 parts (100%) of 3-(3-fluorophenyl)piperidine hydrochloride as a residue (intermediate 93).

In a similar manner there were also prepared:

4-(2-thienyl)piperidine hydrochloride (intermediate 94); and 3-(3-methylphenyl)pyrrolidine hydrochloride as a residue (intermediate 95).

Example 18

A mixture of 21 parts of N-(3-methylphenyl)-1-(phenylmethyl)-4-piperidinamine dihydrochloride, 9 parts of poly(oxymethylene), 15 parts of potassium acetate, 2 parts of a solution of thiophene in methanol 4% and 200 parts of methanol was hydrogenated at normal pressure and at room temperature with 4 parts of palladium-on-charcoal catalyst 10%. After the calculated amount of hydrogen was taken up, the catalyst was filtered off over Hyflo and the filtrate was evaporated. From the residue, the free base was liberated with ammonium hydroxide and extracted with dichloromethane. The extract was dried, filtered and evaporated. The residue was purified by column chromatography over silica gel using a mixture of trichloromethane and methanol (99:1 by volume) as eluent. The pure fractions were collected and the eluent was evaporated. The residue was converted into the hydrochloride salt in 2-propanol. The salt was filtered off and dried, yielding 2.4 parts (75%) of N-methyl-N-(3-methylphenyl)-1-(phenylmethyl)-4-piperidinamine dihydrochloride hemihydrate; mp. 201.3° C. (intermediate 96).

A mixture of 9 parts of N-methyl-N-(3-methylphenyl)-1-(phenylmethyl)-4-piperidinamine dihydrochloride hemihydrate and 200 parts of methanol was hydrogenated at normal pressure and at room temperature with 2 parts of palladium-on-charcoal catalyst 10%. After the calculated amount of hydrogen was taken up, the catalyst was filtered off over Hyflo and the filtrate was evaporated. The residue Was converted into the hydrochloride salt in 2-propanol. The salt was filtered off and dried, Yielding 1.5 parts (60.9%) of N-methyl-N-(3-methylphenyl)-4-piperidinamine dihydrochloride monohydrate; mp. 209.1° C. (intermediate 97).

B. Preparation of Final compounds

Example 19

A mixture of 47.6 parts of 1H-imidazole, 33.6 parts of sodium hydride dispersion 50% and 750 parts of N,N-dimethylformamide was stirred at room temperature for 15 minutes. The resulting solution was added to 106 parts of 3,6-dichloropyridazine in 750 parts of N,N-dimethylformamide and the whole was further stirred for 2 days at room temperature. The product was extracted with trichloromethane. The extract was dried, filtered and evaporated. The residue was crystallized from methanol. The product was filtered off, washed with petroleumether and dried, yielding 48.5 parts of 3-chloro-6-(1H-imidazol-1-yl)pyridazine: mp. 182.9° C. (compound 1).

Example 20

A mixture of 3 parts of 3.5-dimethylphenol, 1.25 parts of sodium hydride dispersion 50% and 25 parts of N,N-dimethylformamide was stirred for 15 minutes. Then there was added a solution of 4.5 parts of 3-chloro-6-(1H--imidazol-1-yl)pyridazine in 25 parts of N,N-dimethylformamide and the whole was stirred over weekend at 50° C. The reaction mixture was poured onto water and the product was extracted with trichloromethane. The extract was dried, filtered and evaporated. The residue was crystallized from 2-propanone, yielding 3.5 parts of 3-(3.5-dimethylphenoxy)-6-(1H-imidazol-1-yl)pyridazine; mp. 169.8° C. (compound 2).

In a similar manner there were also prepared:
3-(1H-imidazol-1-yl)-6-(4-methylphenoxy)pyridazine; mp. 146.8° C. (compound 3);
3-(1H-imidazol-1-yl)-6-(3-nitrophenoxy)pyridazine; mp. 171.5° C. (compound 4); and
3-(4-chlorophenoxy)-6-(1H--imidazol-1-yl)-pyridazine; mp. 165.8° C. (compound 5).

Example 21

A mixture of 4.5 parts of 3-chloro-6-(1H-imidazol-1-yl)pyridazine, 3.2 parts of 4-bromophenol, 4.2 parts of sodium carbonate and 80 parts of 2-propanone was stirred and refluxed over weekend. The reaction mixture was evaporated and the residue was taken up in water and 2.2'-oxybispropane. The layers were separated. The organic phase was dried, filtered and evapoated. The residue was crystallized from 2-propanol, yielding 3.5 parts of 3-(4-bromophenoxy)-6-(1H-imidazol-1-yl)pyridazine; mp. 168.4° C. (compound 6).

Example 22

A mixture of 4.35 parts of 1-(4-fluorophenyl)-4-oxocyclohexanecarbonitrile, 3.3 parts of 1-(3-piperazinyl)pyridazine, 0.2 parts of 4-methylbenzenesulfonic acid and 360 parts of methylbenzene was stirred and refluxed overnight using a water separator. The reaction mixture was cooled and evaporated, yielding 7.3 parts (100%) of 1-(4-fluorophenyl)- 4-[4-(3-pyridazinyl)-1-piperazinyl]-3-cyclohexenecarbonitrile as a residue (compound 7).

To a stirred mixture of 7.3 parts of 1-(4-fluorophenyl)-4-[4-(3-pyridazinyl)-1-piperazinyl]-3-cyclohexenecarbonitrile, 1 part of sodium methoxide solution 30% and 240 parts of methanol were added portionwise 0.8 parts of sodium borohydride. Upon completion, stirring was continued overnight at room temperature. The reaction mixture was poured onto ice water and the product was extracted with trichloromethane. The extract was dried, filtered and evaporated. The residue was crystallized from 2-propanol. Yielding 4.5 parts (61.5%) of 1-(4-fluorophenyl)-4-[4-(3-pyridazinyl)-1-piperazinyl]cyclohexanecarbonitrile; mp. 188.7° C. (compound 8).

Example 23

A mixture of 3.1 parts of 3,6-dichloropyridazine, 3 parts of 1-(2-fluorophenyl)piperazine. 3.2 parts of sodium carbonate, 0.1 parts of potassium iodide and 72 parts of N,N-dimethylformamide was stirred and heated over weekend at 60° C. The reaction mixture was poured into water. The precipitated product Was filtered off and dissolved in trichloromethane. The organic layer was dried, filtered and evaporated. The residue was purified by filtration over silica gel using a mixture of trichloromethane and methanol (98:2 by volume) as eluent. The pure fractions were collected and the eluent was evaporated. The residue was crystallized from a mixture of 2-propanol and 2,2'-oxybispropane, yielding 4.5 parts (77%) of 3-chloro-6-[4-(2-fluorophenyl)-1-piperazinyl]pyridazine; mp. 148.0° C. (compound 9).

Following the same procedure and using equivalent amounts of the appropriate starting materials, there were also prepared:

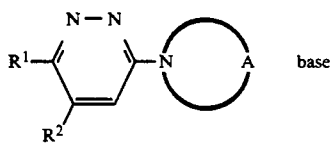

| No. | R¹ | R² | A | mp. in °C. |
|---|---|---|---|---|
| 10 | Cl | H | $(CH_2)_2-N-(2-C_2H_5-C_6H_4)$ / $(CH_2)_2$ | 107.9 |
| 11 | N=\\N-/ | H | $(CH_2)_2-N-(3-CH_3-C_6H_4)$ / $(CH_2)_2$ | 177.7 |
| 12 | Cl | H | $(CH_2)_2-N-(3-C_2H_5-C_6H_4)$ / $(CH_2)_2$ | 119.8 |
| 13 | Cl | H | $(CH_2)_2-N-(5-CH_3-2-pyridinyl)$ / $(CH_2)_2$ | 226.2 |
| 14 | Cl | $CH_3$ | $(CH_2)_2-N-(3-CH_3-C_6H_4)$ / $(CH_2)_2$ | 152.7 |
| 15 | Cl | H | $(CH_2)_2-N-[2,4,6-(CH_3)_3-C_6H_2]$ / $(CH_2)_2$ | 149.8 |
| 16 | Cl | $CH_3$ | $(CH_2)_2-N-(3-Cl-C_6H_4)$ / $(CH_2)_2$ | 163.5 |
| 17 | Cl | H | $(CH_2)_2-N-(2-Br-C_6H_4)$ / $(CH_2)_2$ | 191.4 |
| 18 | Cl | H | $(CH_2)_2-CH-NH-(3-CH_3-C_6H_4)$ / $(CH_2)_2$ | 156.8 |
| 19 | Cl | H | $(CH_2)_2-N-(2,3-Cl_2-C_6H_3)$ / $(CH_2)_2$ | 160.6 |
| 20 | Cl | $CH_3$ | $(CH_2)_2-N-(3-CF_3-C_6H_4)$ / $(CH_2)_2$ | 176.6 |
| 21 | Cl | H | $(CH_2)_2-CH-C_6H_5$ / $(CH_2)_2$ | 122.7 |
| 22 | Cl | H | $(CH_2)_2-CH-(3-CH_3-C_6H_4)$ / $(CH_2)_2$ | 107.5 |
| 23 | Cl | H | $(CH_2)_2-CH-(3-CF_3-C_6H_4)$ / $(CH_2)_2$ | 69.8 |

Example 24

A mixture of 2.7 parts of 3,6-difluoropyridazine, 4.6 parts of 1-[3-(trifluoromethyl)phenyl]piperazine, 3.2 parts of sodium carbonate and 90 parts of N,N-dimethylformamide was stirred overnight at 60° C. The reaction mixture was poured into water. The product was filtered off, washed with water and crystallized from 2-propanol, yielding 3 parts (46%) of 3-fluoro-6-[4-[3-(trifluoromethyl)phenyl]-1-piperazinyl]pyridazine; mp. 131.5° C. (compound 24).

In a similar manner there were also prepared:
3-[4-(2,3-dimethylphenyl)-1-piperazinyl]-6-fluoropyridazine; mp. 144.1° C. (compound 25);
3-fluoro-6-[4-(3-methylphenyl)-1-piperazinyl]pyridazine: mp. 128.1° C. (compound 26) and 3-[3,6-dihydro-4-(3-methylphenyl)-1(2H)-pyridinyl]-6-fluoropyridazine; mp. 105.2° C. (compound 27).

Example 25

A mixture of 4.5 parts of 3,6-dichloropyridazine, 5.2 parts of 1,2,3,6-tetrahydro-4-(3-methylphenyl)pyridine, 5.3 parts of sodium carbonate and 72 parts of N,N-dimethylformamide was stirred and heated overnight at about 70° C. The reaction mixture was evaporated and water was added to the residue. The product was extracted with trichloromethane. The extract was dried, filtered and evaporated. The residue was purified by filtration over silica gel using a mixture of trichloromethane and methanol (98:2 by volume) as eluent. The pure fractions were collected and the eluent was evaporated. The residue was crystallized from 2-propanol. The product was filtered off and dried, yielding 2.1 parts (24%) of 3-chloro-6-[3,6-dihydro-4-(3-methylphenyl)-1(2H)-pyridinyl]pyridazine: mp. 122.2° C. (compound 28).

Following the same procedure and using equivalent amounts of the appropriate starting materials, there were also prepared:

|  | $R^1$ | A | Salt or base | mp. in °C. |
|---|---|---|---|---|
| 29 | Cl | (CH$_2$)$_2$—N—(4-CH$_3$O—C$_6$H$_4$)<br>        \|<br>      (CH$_2$)$_2$ | base | 183.3 |
| 30 | Cl | CH$_2$—CH(CH$_3$)—N—(4-CH$_3$O—C$_6$H$_4$)<br>              \|<br>           (CH$_2$)$_2$ | base | 133.5 |
| 31 | Cl | (CH$_2$)$_2$—N—(2-thiazolyl)<br>        \|<br>      (CH$_2$)$_2$ | base | 221.9 |
| 32 | Cl | (CH$_2$)$_2$—N—(3-Cl—C$_6$H$_4$)<br>        \|<br>      (CH$_2$)$_2$ | base | 146.6 |
| 33 | Cl | (CH$_2$)$_2$—N—C$_6$H$_5$<br>        \|<br>      (CH$_2$)$_2$ | base | 172.0 |
| 34 | Cl | (CH$_2$)$_2$—N—(2-CH$_3$O—C$_6$H$_4$)<br>        \|<br>      (CH$_2$)$_2$ | base | 144.5 |
| 35 | Cl | (CH$_2$)$_2$—N—(4-CH$_3$—C$_6$H$_4$)<br>        \|<br>      (CH$_2$)$_2$ | base | 188.6 |
| 36 | Cl | (CH$_2$)$_2$—N—[3,4-(CH$_3$)$_2$—C$_6$H$_3$]<br>        \|<br>      (CH$_2$)$_2$ | base | 162.6 |
| 37 | Cl | (CH$_2$)$_2$—N—(2-pyrimidinyl)<br>        \|<br>      (CH$_2$)$_2$ | base | 207.7 |
| 38 | Cl | (CH$_2$)$_2$—N—[2,3-(CH$_3$)$_2$—C$_6$H$_3$]<br>        \|<br>      (CH$_2$)$_2$ | base | 164.6 |
| 39 | Cl | (CH$_2$)$_2$—N—(3-CH$_3$—C$_6$H$_4$)<br>        \|<br>      (CH$_2$)$_2$ | base | 140.1 |
| 40 | Cl | CH$_2$—CH(CH$_3$)—N—(2-Cl—C$_6$H$_4$)<br>              \|<br>           (CH$_2$)$_2$ | base | 118.2 |
| 41 | Cl | (CH$_2$)$_2$—N—(4-C$_2$H$_5$OC(O)—C$_6$H$_4$)<br>        \|<br>      (CH$_2$)$_2$ | base | 200.6 |
| 42 | Cl | (CH$_2$)$_2$—N—[2,4-(CH$_3$)$_2$—C$_6$H$_3$]<br>        \|<br>      (CH$_2$)$_2$ | base | 155.8 |

-continued

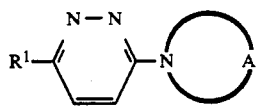

| | R¹ | A | Salt or base | mp. in °C. |
|---|---|---|---|---|
| 43 | Cl | CH₂—CH(CH₃)—N—(4-CH₃—C₆H₄)<br>                    \|<br>                    (CH₂)₂ | base | 124.4 |
| 44 | Cl | (CH₂)₂—N—(2-CH₃O,5-CF₃—C₆H₃)<br>        \|<br>    (CH₂)₂ | base | 160.0 |
| 45 | Cl | (CH₂)₂—N—CH(C₆H₅)₂<br>       \|<br>    (CH₂)₂ | base | 156.4 |
| 46 | Cl | CH₂—CH(CH₃)—N—(3-CH₃—C₆H₄)<br>                    \|<br>                    (CH₂)₂ | base | 114.8 |
| 47 | Cl | (CH₂)₂—N—(3-F—C₆H₄)<br>       \|<br>    (CH₂)₂ | base | 153.1 |
| 48 | Cl | (CH₂)₂—N—(3-CN-2-pyridinyl)<br>       \|<br>    (CH₂)₂ | base | 177.3 |
| 49 | Cl | (CH₂)₂—N—C₆H₄—C(O)—(4-Cl—C₆H₄)<br>       \|<br>    (CH₂)₂ | base | 262.5 |
| 50 | Cl | CH₂—CH(CH₃)—N—(4-Cl—C₆H₄)<br>                    \|<br>                    (CH₂)₂ | base | 161.3 |
| 51 | Cl | (CH₂)₂—N—[3,4-(CH₃O)₂—C₆H₃]<br>       \|<br>    (CH₂)₂ | base | 149.5 |
| 52 | Cl | CH₂—CH(CH₃)—N—C₆H₅<br>                    \|<br>                    (CH₂)₂ | base | 145.9 |
| 53 | Cl | (CH₂)₂—N—(4-OH—C₆H₄)<br>       \|<br>    (CH₂)₂ | base | 203.5 |
| 54 | Cl | (CH₂)₂—CH—NH—C₆H₅<br>       \|<br>    (CH₂)₂ | base | 149.6 |
| 55 | Cl | (CH₂)₂—N—(3,5-Cl₂—C₆H₃)<br>       \|<br>    (CH₂)₂ | base | 167.2 |
| 56 | Cl | (CH₂)₂—N—[3,5-(CH₃)₂—C₆H₃]<br>       \|<br>    (CH₂)₂ | base | 164.7 |
| 57 | Cl | CH₂—CH—NH—[2,3-(CH₃)₂—C₆H₃]<br>       \|<br>    (CH₂)₃ | HCl | 218.0 |
| 58 | Cl | CH₂—CH—NH—(3-CH₃—C₆H₄)<br>       \|<br>    (CH₂)₂ | base | 161.9 |
| 59 | Cl | CH₂—CH—NH—C₆H₅<br>       \|<br>    (CH₂)₃ | HCl | 142.2 |

-continued

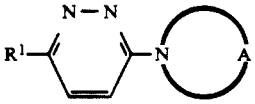

| | R¹ | A | Salt or base | mp. in °C. |
|---|---|---|---|---|
| 60 | Cl | (CH₂)₃—N—(3-Cl—C₆H₄)<br>  \|<br>  (CH₂)₂ | base | 123.0 |
| 61 | Cl | CH₂—CH—NH—(3-CH₃—C₆H₄)<br>      \|<br>      (CH₂)₃ | HCl | 176.5 |
| 62 | Cl | (CH₂)₂—N—(2,4-Cl₂C₆H₃)<br>  \|<br>  (CH₂)₂ | base | 185.2 |
| 63 | Cl | (CH₂)₃—N—[2,3-(CH₃)₂C₆H₃]<br>  \|<br>  (CH₂)₂ | base | 118.8 |
| 64 | Cl | (CH₂)₃—N—(3,5-Cl₂—C₆H₃)<br>  \|<br>  (CH₂)₂ | base | 174.9 |
| 65 | Cl | C₆H₅<br>  \|<br>(CH₂)₂—C—C(O)—NH—C₆H₅<br>  \|<br>  (CH₂)₂ | base | 224.4 |
| 66 | Cl | (CH₂)₂—CH—N(CH₃)(3-CH₃C₆H₄)<br>      \|<br>      (CH₂)₂ | base | 136.5 |
| 67 | Cl | OH<br>  \|<br>(CH₂)₂—C—CH₂—(4-Cl—C₆H₄)<br>  \|<br>  (CH₂)₂ | base | 172.9 |
| 68 | Cl | OCH₃<br>  \|<br>(CH₂)₂—C—C₆H₅<br>  \|<br>  (CH₂)₃ | base | 147.6 |
| 69 | Cl | OH<br>  \|<br>(CH₂)₂—C—(3-CF₃—C₆H₄)<br>  \|<br>  (CH₂)₂ | HCl | 194.5 |
| 70 | Cl | CH₂—NH—C(O)—CH₃<br>  \|<br>(CH₂)₂—C—(4-CH₃—C₆H₄)<br>  \|<br>  (CH₂)₂ | base | 221.8 |
| 71 | Cl | CH₃<br>  \|<br>(CH₂)₂—CH—N—CH₂—CH=CH—C₆H₅<br>      \|<br>      (CH₂)₂ | base | 95.2 |
| 72 | Cl | OH<br>  \|<br>(CH₂)₂—C—(3-Br-4-Cl—C₆H₃)<br>  \|<br>  (CH₂)₂ | base | 199.6 |
| 73 | Cl | CH₂—CH—NH—C₆H₅<br>      \|<br>      (CH₂)₂ | base | 167.9 |
| 74 | Cl | (CH₂)₂—CH—O—C(O)—C₆H₅<br>      \|<br>      (CH₂)₂ | base | 120.9 |

-continued

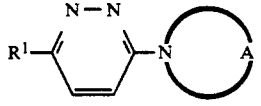

| | R¹ | A | Salt or base | mp. in °C. |
|---|---|---|---|---|
| 75 | Cl | (CH₂)₂—C(CH₃)(CH₂)₂—CH₂—CH₃ | base | 80.4 |
| 76 | Cl | (CH₂)₂—C(C(O)—OCH₃)(CH₂)₂—NH—(3-CF₃—C₆H₄) | base | 119.0 |
| 77 | Cl | CH₂—CH=C(CH₂)₂—(3-CF₃—C₆H₄) | base | 120.8 |
| 78 | Cl | (CH₂)₂—C(C₆H₅)(CH₂)₂—C₆H₅ | base | 178.7 |
| 79 | Cl | (CH₂)₂—C(OH)(CH₂)₂—(3-CH₃—C₆H₄) | base | 140.4 |
| 80 | Cl | CH₂—CH(CH₂)₂—NH—[(2,3-CH₃)₂C₆H₃] | base | 163.2 |
| 81 | Cl | (CH₂)₂—N(CH₂)₂—(2-CH₃—C₆H₄) | base | 148.0 |
| 82 | Cl | (CH₂)₂—C(C(O)—NH₂)(CH₂)₂—(3-CH₃—C₆H₄) | base | 237.8 |
| 83 | Cl | (CH₂)₂—CH(CH₂)₂—CO—(3-CF₃—C₆H₄) | base | 126.0 |
| 84 | Cl | (CH₂)₃—N(CH₂)₂—(3-CH₃O—C₆H₄) | HCl | 173.8 |
| 85 | Cl | (CH₂)₂—CH(CH₂)₂—(4-CH₃—C₆H₄) | base | 127.9 |
| 86* | Cl | CH₂—CH(CH₃)—C(OH)(CH₂)₂—(3-CF₃—C₆H₄) | base | 163.8 |
| 87 | Cl | (CH₂)₂—C(OH)(CH₂)₂—(2-thienyl) | base | 162.7 |
| 88 | Cl | CH₂—CH(CH₂)₂—NH—(3-CF₃—C₆H₄) | base | 152.0 |
| 89 | Cl | (CH₂)₂—N(CH₂)₂—(2-quinolinyl) | base | 207.7 |

-continued $$R^1-\underset{N-N}{\underset{\|}{\bigcirc}}-N\underset{A}{\bigcirc}$$

| | $R^1$ | A | Salt or base | mp. in °C. |
|---|---|---|---|---|
| 90 | Cl | (CH$_2$)$_2$—C—(2-thienyl)<br>‖<br>CH$_2$—CH | base | 156.4 |
| 91 | Cl | CH$_2$—CH—(4-Cl—C$_6$H$_4$)<br>\|<br>(CH$_2$)$_3$ | base | 118.9 |
| 92 | Cl | OH<br>\|<br>(CH$_2$)$_2$—C—(3-Cl—C$_6$H$_4$)<br>\|<br>(CH$_2$)$_2$ | base | 206.0 |
| 93 | Cl | (CH$_2$)$_2$—CH—O—(4-F—C$_6$H$_4$)<br>\|<br>(CH$_2$)$_2$ | base | 147.0 |
| 94 | Cl | (CH$_2$)$_2$—C—(4-Cl,3-CF$_3$—C$_6$H$_3$)<br>‖<br>CH$_2$—CH | base | 137.5 |
| 95 | Cl | OH<br>\|<br>(CH$_2$)$_2$—C—(3-CH$_3$O—C$_6$H$_4$)<br>\|<br>(CH$_2$)$_2$ | base | 134.7 |
| 96 | Cl | (CH$_2$)$_2$—N—CH$_2$—(2-CH$_3$—C$_6$H$_4$)<br>\|<br>(CH$_2$)$_2$ | base | 134.7 |
| 97* | Cl | OH<br>\|<br>CH$_2$—CH(CH$_3$)—C—(3-CH$_3$—C$_6$H$_4$)<br>\|<br>(CH$_2$)$_2$ | base | 154.0 |
| 98 | Cl | (CH$_2$)$_2$—CH—NH—(3-Cl—C$_6$H$_4$)<br>\|<br>(CH$_2$)$_2$ | base | 153.3 |
| 99* | Cl | OH<br>\|<br>CH$_2$—CH(CH$_3$)—C—(3-F—C$_6$H$_4$)<br>\|<br>(CH$_2$)$_2$ | base | 160.5 |
| 100* | Cl | OH<br>\|<br>CH$_2$—CH(CH$_3$)—C—(2-thienyl)<br>\|<br>(CH$_2$)$_2$ | base | 148.1 |
| 101 | Cl | (CH$_2$)$_2$—CH—(1H-indol-3-yl)<br>\|<br>(CH$_2$)$_2$ | base | 182.7 |
| 102 | Cl | OH<br>\|<br>(CH$_2$)$_2$—C—(3-F—C$_6$H$_4$)<br>\|<br>(CH$_2$)$_2$ | base | 156.8 |
| 103 | Cl | OH<br>\|<br>(CH$_2$)$_2$—C—[2,3-(CH$_3$)$_2$—C$_6$H$_3$]<br>\|<br>(CH$_2$)$_2$ | base | 175.0 |
| 104 | Cl | OH<br>\|<br>(CH$_2$)$_2$—C—(1-naphthalenyl)<br>\|<br>(CH$_2$)$_2$ | base | 201.8 |

-continued $$R^1 \underset{\underset{}{\bigg|}}{\overset{N=N}{\diagup}} \underset{N}{\diagdown} A$$

| | $R^1$ | A | Salt or base | mp. in °C. |
|---|---|---|---|---|
| 105 | Cl | CH$_2$—CH(CH$_3$)—C(OH)(CH$_2$)$_2$—(3-Cl—C$_6$H$_4$) | HCl | 200 |
| 106 | Cl | (CH$_2$)$_2$—C(OH)(CH$_2$)$_2$—(4-Cl,3-CF$_3$—C$_6$H$_3$) | base | 208.4 |
| 107 | Cl | (CH$_2$)$_2$—C(OH)(CH$_2$)$_2$—(4-Br—C$_6$H$_4$) | base | 169.4 |
| 108 | Cl | (CH$_2$)$_2$—C(OH)(CH$_2$)$_2$—(CH$_2$)$_3$—C$_6$H$_5$ | base | 105.1 |
| 109 | Cl | (CH$_2$)$_2$—C(OH)(CH$_2$)$_2$—(4-Cl—C$_6$H$_4$) | base | 161.5 |
| 110 | Cl | (CH$_2$)$_2$—C(OH)(CH$_2$)$_2$—(4-CH$_3$—C$_6$H$_4$) | base | 123.1 |
| 111 | Cl | (CH$_2$)$_2$—C(OH)(CH$_2$)$_2$—(4-F—C$_6$H$_4$) | base | 156.6 |
| 112 | Cl | (CH$_2$)$_2$—C(1-naphthalenyl)=CH—CH$_2$ | base | 138.4 |
| 113 | CH$_3$O—C(=O) | (CH$_2$)$_2$—N(CH$_2$)$_2$—(3-CH$_3$—C$_6$H$_4$) | base | 185.5 |
| 114 | Cl | (CH$_2$)$_2$—C(OH)(CH$_2$)$_2$—[4-CH(CH$_3$)$_2$—C$_6$H$_4$] | base | 136.5 |
| 115 | Cl | (CH$_2$)$_2$—C(OH)(CH$_2$)$_2$—(CH$_2$)$_4$—C$_6$H$_5$ | base | 106.2 |
| 116 | Cl | (CH$_2$)$_2$—C(OH)(CH$_2$)$_2$—(CH$_2$)$_2$—C$_6$H$_5$ | base | 147.3 |
| 117 | Cl | (CH$_2$)$_2$—C(OH)(CH$_2$)$_2$—(2-naphthalenyl) | base | 196.1 |

-continued

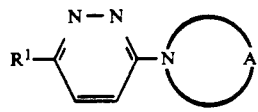

| | R¹ | A | Salt or base | mp. in °C. |
|---|---|---|---|---|
| 118 | Cl | (CH₂)₂—N(—(CH₂)₂)—(4-NO₂—C₆H₄) | HCl.½H₂O | 266.7 |
| 119 | Cl | (CH₂)₂—C(OH)(—(CH₂)₂)—(4-CH₃O—C₆H₄) | base | 173.7 |
| 120 | NC | (CH₂)₂—N(—(CH₂)₂)—(3-CH₃—C₆H₄) | base | 179.8 |
| 121 | Cl | (CH₂)₂—C(=CH—CH₂)—(4-Cl—C₆H₄) | base | 204.5 |
| 122 | Cl | CH₂—CH(CH₃)—C(—(CH₂)₂)—(3-OCH₃—C₆H₄) | HCl | 196.1 |
| 123 | Cl | (CH₂)₂—C(OH)(—(CH₂)₂)—CH₃ | base | 125.1 |
| 124 | CH₃OOC | (CH₂)₂—C(=CH—CH₂)—(3-CH₃—C₆H₄) | base | 159.6 |
| 125 | (imidazolyl) | (CH₂)₂—C(=CH—CH₂)—(3-CH₃—C₆H₄) | base | 164.8 |
| 126 | Cl | (CH₂)₂—N(—(CH₂)₂)—(1-naphthalenyl) | base | 156.6 |
| 127 | CH₃OOC | (CH₂)₂—C(OH)(—(CH₂)₂)—(3-CH₃—C₆H₄) | base | — |
| 128 | Cl | CH₂—C(=CH—CH₂)—(2-thienyl) | base | 210.7 |
| 129 | I | (CH₂)₂—C(=CH—CH₂)—(3-CH₃—C₆H₄) | base | 145.4 |
| 130 | CN | (CH₂)₂—C(=CH—CH₂)—(3-CH₃—C₆H₄) | base | 138.0 |
| 131 | Cl | (CH₂)₂—C(—(CH₂)₂)—(2-pyridinyl) | base | — |
| 132 | Cl | (CH₂)₂—C(=CH—CH₂)—(2-pyridinyl) | base | — |
| 133 | Cl | (CH₂)₂—C(=CH—CH₂)—CH₃ | base | — |

| | | | Salt or base | mp. in °C. |
|---|---|---|---|---|
| 134 | Cl | (CH₂)₂—C—(CH₂)₃—CH₃<br>‖<br>CH₂—CH | base | — |

*cis form

In a similar manner there was also prepared: ethyl 4-(6-chloro-5-methyl-3-pyridazinyl)-1-piperazinecarboxylate; mp. 132.2° C. (compound 135).

Example 26

A mixture of 5 parts of 1-(3-methylphenyl)piperazine dihydrochloride, 10.6 parts of sodium carbonate and 180 parts of N,N-dimethylformamide was stirred for 1 hour at 65° C. Then there were added 7.2 parts of 3,6-dibromopyridazine and the whole was stirred overnight at about 65° C. The reaction mixture was poured into ice water. The product was filtered off and dissolved in dichloromethane. The solution was washed twice with water, dried, filtered and evaporated. The residue was crystallized from ethanol. The product was filtered off and dried, yielding 4.1 parts (61.5%) of 3-bromo-6-[4-(3-methylphenyl)-1-piperazinyl]pyridazine: mp. 145.7° C. (compound 136).

In a similar manner there were also prepared:

3-bromo-6-[4-(2,3-dimethylphenyl)-1-piperazinyl]-pyridazine; mp. 166.7° C. (compound 137);

3-bromo-6-[4-(3-chlorophenyl)-1-piperazinyl]pyridazine; mp. 158.7° C. (compound 138);

3-bromo-6-[4-[3-(trifluoromethyl)phenyl]-1-piperazinyl)pyridazine; mp. 154.3° C. (compound 139);

3-bromo-6-[4-(2-methoxyphenyl)-1-piperazinyl]-pyridazine; mp. 164.8° C. (compound 140);

3-bromo-6-[4-[3-(trifluoromethyl)phenyl]-1-piperidinyl]pyridazine monohydrochloride: mp. 222.5° C. (compound 141);

3-bromo-6-[3,6-dihydro-4-[3-(trifluoromethyl)-phenyl]-1(2H)-pyridinyl]-pyridazine; mp. 130.6° C. (compound 142);

1-(6-bromo-3-pyridazinyl)-4-(3-chlorophenyl)-hexahydro-1H-1,4-diazepine; mp. 148.8° C. (compound 143);

3-bromo-6-[4-(3-bromophenyl)-1-piperazinyl]pyridazine; mp. 179.8° C. (compound 144); and 3-bromo-6-[3.6-dihydro-4-(3-methylphenyl)-1(2H)-pyridinyl]-pyridazine; mp. 127.1° C. (compound 145);

Example 27

A mixture of 4.5 parts of 3,6-dichloropyridazine, 4.9 parts of N-[3-(trifluoromethyl)phenyl]-3-piperidinamine, 6.4 parts of sodium carbonate and 180 parts of N,N-dimethylformamide was stirred overnight at about 65° C. The reaction mixture was poured into ice water and the product was extracted with dichloromethane. The extract was dried, filtered and evaporated. The residue was purified by column chromatography over silica gel using a mixture of trichloromethane and methanol (99:1 by volume) as eluent. The pure fractions were collected and the eluent was evaporated. The residue was crystallized from 2-propanol. The product was filtered off (the filtrate was set aside) and dried, yielding 1.2 parts (16.8%) of 1-(6-chloro-3-pyridazinyl)-N-[3-(trifluoromethyl)phenyl]-3-piperidinamine: mp. 92.6° C. (compound 146). The filtrate, which was set aside, was converted into the hydrochloride salt in 2-propanol. The salt was filtered off and dried, yielding 2.6 parts (32.9%) of 1-(6-chloro-3-pyridazinyl)-N-[3-(trifluoromethyl)-phenyl]-3-piperidinamine monohydrochloride; mp. 173.5° C. (compound 147).

Example 28

A mixture of 3 parts of 3,6-dichloropyridazine, 6.1 parts of N-[3-(trifluoromethyl)phenyl]-4-piperidinamine dihydrobromide, 6.4 parts of sodium carbonate and 180 parts of N,N-dimethylacetamide was stirred for 24 hours at 60° C. After cooling to room temperature, the reaction mixture was poured onto water. The product was extracted with methylbenzene. The extract was washed with water, dried, filtered and evaporated. The residue was purified by column chromatography over silica gel using a mixture of trichloromethane and methanol (97:3 by volume) as eluent. The pure fractions were collected and the eluent was evaporated. The residue was crystallized from 2,2'-oxybispropane. The product was filtered off and dried, yielding 2.5 parts (47%) of 1-(6-chloro-3-pyridazinyl)-N-[3-(trifluoromethyl)-phenyl]-4-piperidinamine; mp. 117.9° C. (compound 148).

Following the same procedure and using equivalent amounts of the appropriate starting materials, there were also prepared:

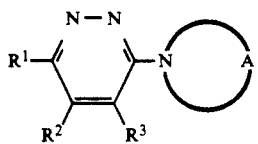

| No. | $R^1$ | $R^2$ | $R^3$ | A | Salt or base | mp. in °C. |
|---|---|---|---|---|---|---|
| 149 | Cl | H | H | $(CH_2)_2-N-(4\text{-}Cl-C_6H_4)$<br>$\quad\quad\;\;\;\|$<br>$(CH_2)_2$ | base | 209.7 |
| 150 | Cl | H | H | $(CH_2)_2-N-(2\text{-}Cl-C_6H_4)$<br>$\quad\quad\;\;\;\|$<br>$(CH_2)_2$ | base | 184.7 |
| 151 | Cl | H | H | $(CH_2)_2-N-(3\text{-}CH_3O-C_6H_4)$<br>$\quad\quad\;\;\;\|$<br>$(CH_2)_2$ | base | 127.0 |
| 152 | Cl | H | H | $(CH_2)_2-N-(4\text{-}F-C_6H_4)$<br>$\quad\quad\;\;\;\|$<br>$(CH_2)_2$ | base | 197.4 |
| 153 | Cl | H | H | $(CH_2)_2-N-(3,4\text{-}Cl_2-C_6H_3)$<br>$\quad\quad\;\;\;\|$<br>$(CH_2)_2$ | base | 160.5 |
| 154 | Cl | H | H | $(CH_2)_2-N-[2,6\text{-}(CH_3)_2-C_6H_3]$<br>$\quad\quad\;\;\;\|$<br>$(CH_2)_2$ | base | 124.4 |
| 155 | Cl | $-CH=CH-CH=CH-$ | | $(CH_2)_2-N-[2,3\text{-}(CH_3)_2-C_6H_3]$<br>$\quad\quad\;\;\;\|$<br>$(CH_2)_2$ | base | 209.2 |
| 156 | Cl | $-CH=CH-CH=CH-$ | | $(CH_2)_2-N-(2\text{-}CH_3O-C_6H_4)$<br>$\quad\quad\;\;\;\|$<br>$(CH_2)_2$ | base | 178.6 |
| 157 | Cl | $-CH=CH-CH=CH-$ | | $(CH_2)_2-N-C_6H_5$<br>$\quad\quad\;\;\;\|$<br>$(CH_2)_2$ | base | 170.2 |
| 158 | Cl | $-CH=CH-CH=CH-$ | | $(CH_2)_2-N-(3\text{-}CF_3-C_6H_4)$<br>$\quad\quad\;\;\;\|$<br>$(CH_2)_2$ | base | 167.2 |
| 159 | Cl | $-CH=CH-CH=CH-$ | | $(CH_2)_2-N-(3\text{-}Cl-C_6H_4)$<br>$\quad\quad\;\;\;\|$<br>$(CH_2)_2$ | base | 167.0 |
| 160 | Cl | $-CH=CH-CH=CH-$ | | $(CH_2)_2-N-(3\text{-}CH_3-C_6H_4)$<br>$\quad\quad\;\;\;\|$<br>$(CH_2)_2$ | base | 135.6 |
| 161 | Cl | $-CH=CH-CH=CH-$ | | $(CH_2)_2-N-(3,5\text{-}Cl_2-C_6H_3)$<br>$\quad\quad\;\;\;\|$<br>$(CH_2)_2$ | base | 225.6 |
| 162 | Cl | H | H | $\quad\quad\quad\;\;$ OH<br>$\quad\quad\quad\;\;\;\|$<br>$(CH_2)_2-C-(3,4\text{-}Cl_2-C_6H_3)$<br>$\quad\quad\;\;\;\|$<br>$(CH_2)_2$ | base | 196.3 |
| 163 | Cl | H | H | $\quad\quad\quad\;\;$ C(O)O$-CH_2CH_3$<br>$\quad\quad\quad\;\;\;\|$<br>$(CH_2)_2-C-(3\text{-}Cl-C_6H_4)$<br>$\quad\quad\;\;\;\|$<br>$(CH_2)_2$ | base | 155.5 |
| 164 | Cl | H | H | $\quad\quad\quad\;\;$ C(O)$-NH_2$<br>$\quad\quad\quad\;\;\;\|$<br>$(CH_2)_2-C-NH-(3\text{-}CH_3-C_6H_4)$<br>$\quad\quad\;\;\;\|$<br>$(CH_2)_2$ | base | 195.1 |

-continued

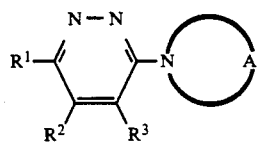

| No. | R¹ | R² | R³ | A | Salt or base | mp. in °C. |
|---|---|---|---|---|---|---|
| 165 | Cl | H | H | (CH$_2$)$_2$—N—(3-Br—C$_6$H$_4$)<br>              (CH$_2$)$_2$ | base | 157.1 |
| 166 | Cl | H | H |          O—(CH$_2$)$_3$—(1-piperidinyl)<br>(CH$_2$)$_2$—C—C$_6$H$_5$<br>        (CH$_2$)$_2$ | base | 137.1 |
| 167 | Cl | H | H |         (CH$_2$)$_2$—CH$_3$<br>(CH$_2$)$_2$—C—C$_6$H$_5$<br>        (CH$_2$)$_2$ | base | 136.8 |
| 168 | Cl | H | H | CH$_2$—CH—(3-CF$_3$—C$_6$H$_4$)<br>      (CH$_2$)$_2$ | ½ (COOH)$_2$ | 155.2 |
| 169 | Cl | —CH=CH—CH=CH— | | (CH$_2$)$_2$—N—(2,3-Cl$_2$—C$_6$H$_3$)<br>            (CH$_2$)$_2$ | base | 218.5 |
| 170 | Cl | H | H | (CH$_2$)$_3$—N—C$_6$H$_5$<br>         (CH$_2$)$_2$ | base | 132.7 |
| 171 | Cl | H | H | (CH$_2$)$_2$—CH—CO—CH$_2$—C$_6$H$_5$<br>      (CH$_2$)$_2$ | base | 130.2 |
| 172 | Cl | H | H | (CH$_2$)$_3$—CH—(3-CF$_3$—C$_6$H$_4$)<br>      CH$_2$ | base | 121.7 |
| 173 | Cl | H | H | (CH$_2$)$_2$—CH—CH$_2$—CO—(3-F—C$_6$H$_4$)<br>      (CH$_2$)$_2$ | base | 156.2 |
| 174 | Cl | H | H |       OH<br>(CH$_2$)$_2$—C—(3-Cl—C$_6$H$_4$)<br>      CH$_2$ | base | 170.4 |
| 175 | Cl | H | H | (CH$_2$)$_3$—N—(3-CF$_3$—C$_6$H$_4$)<br>         (CH$_2$)$_2$ | base | 144.7 |
| 176 | Cl | H | H |     OH<br>CH$_2$—C—C$_6$H$_5$<br>    (CH$_2$)$_3$ | base | 138.0 |
| 177 | Cl | H | H |     OH<br>CH$_2$—C—(3-CF$_3$—C$_6$H$_4$)<br>    (CH$_2$)$_3$ | base | 95.0 |
| 178 | Cl | H | H |       H<br>(CH$_2$)$_3$—C—C$_6$H$_5$<br>      CH$_2$ | base | 107.5 |
| 179 | Cl | H | H |       H<br>(CH$_2$)$_3$—C—(3-CH$_3$—C$_6$H$_4$)<br>      CH$_2$ | HBr<br>½ CH$_3$—CHOH—CH$_3$ | 193.0 |

-continued

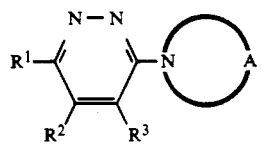

| No. | R¹ | R² | R³ | A | Salt or base | mp. in °C. |
|---|---|---|---|---|---|---|
| 180 | Cl | H | H | (CH₂)₃−C(OH)(CH₂)−(3-CH₃−C₆H₄) | base | 104.4 |
| 181 | Cl | H | H | (CH₂)₃−C(OH)(CH₂)−(2-thienyl) | base | 154.0 |
| 182 | Cl | H | H | (CH₂)₃−C(OH)(CH₂)−(3-Cl−C₆H₄) | base | 121.7 |
| 183 | Cl | H | H | (CH₂)₃−C(H)(CH₂)−(3-F−C₆H₄) | base | 91.5 |
| 184 | Cl | H | H | (CH₂)₃−C(OH)(CH₂)−(3-F−C₆H₄) | base | 119.3 |
| 185 | Br | H | H | (CH₂)₂−N((CH₂)₂)−(CH₂)₃−C₆H₅ | HC−COOH ‖ HOOC−CH | 197.3 |
| 186 | Cl | H | H | (CH₂)₃−C(OH)(CH₂)−[2,3-(CH₃)₂−C₆H₃] | base | 183.7 |
| 187 | Cl | H | H | (CH₂)₃−C(H)(CH₂)−[2,3-(CH₃)₂−C₆H₃] | base | 115.7 |
| 188 | Cl | H | H | (CH₂)₂−C(OH)(CH₂)−(3-CH₃−C₆H₄) | base | 164.4 |
| 189 | Cl | H | H | (CH₂)₂−CH=C(CH₂)−(3-CH₃−C₆H₄) | base | 94.6 |
| 190 | Cl | H | H | (CH₂)₂−CH((CH₂)₂)−(2-thienyl) | base | 127.0 |
| 191 | Cl | H | H | (CH₂)₃−CH(OH)(CH₂)−(3-OCH₃−C₆H₄) | HCl | 193.8 |
| 192 | Cl | H | H | (CH₂)₃−CH(CH₂)−(3-OCH₃−C₆H₄) | base | 102.1 |
| 193 | Cl | H | H | (CH₂)₃−CH(OH)(CH₂)−(4-Cl,3-CF₃−C₆H₃) | base | 129.8 |

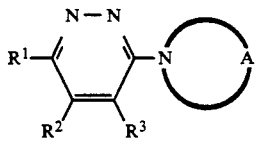

| No. | R¹ | R² | R³ | A | Salt or base | mp. in °C. |
|---|---|---|---|---|---|---|
| 194 | Cl | H | H | (CH$_2$)$_3$—CH=C—(3-F—C$_6$H$_4$)<br>           \|<br>          CH$_2$ | base | 121.5 |
| 195 | Cl | H | H | OH<br>\|<br>(CH$_2$)$_2$—C—(3-F—C$_6$H$_4$)<br>\|<br>CH$_2$ | base | 138.4 |
| 196 | Cl | H | H | (CH$_2$)$_2$—CH—(3-CH$_3$—C$_6$H$_4$)<br>           \|<br>          CH$_2$ | base | 74.7 |
| 197 | Cl | H | H | OH<br>\|<br>(CH$_2$)$_2$—CH—(4-Cl,3-CF$_3$—C$_6$H$_3$)<br>\|<br>CH$_2$ | base | 168.0 |
| 198 | Cl | H | H | OH<br>\|<br>(CH$_2$)$_2$—CH—(3-OCH$_3$—C$_6$H$_4$)<br>\|<br>CH$_2$ | base | 115.1 |
| 199 | Cl | H | H | OH<br>\|<br>(CH$_2$)$_2$—CH—(2-thienyl)<br>\|<br>CH$_2$ | base | 179.5 |
| 200 | Cl | H | H | (CH$_2$)$_2$—CH—NH—COOC$_2$H$_5$<br>           \|<br>          (CH$_2$)$_2$ | base | 157.9 |
| 201 | Cl | H | H | (CH$_2$)$_2$—CH—(2-thienyl)<br>           \|<br>          CH$_2$ | base | 119.3 |

Example 29

A mixture of 5.2 parts of 3,6-diiodopyridazine, 3.5 parts of 1-[3-(trifluoromethyl)phenyl]piperazine, 3.2 parts of sodium carbonate and 90 parts of N,N-dimethylacetamide was stirred and heated overnight at 70° C. The reaction mixture was poured onto water. The precipitated product was filtered off and crystallized from 2-propanol, yielding 3.2 parts (48%) of 3-iodo-6-[4-[3-(trifluoromethyl)phenyl]-1-piperazinyl]-pyridazine; mp. 144.6° C. (compound 202).

In a similar manner there were also prepared:

3-iodo-6-[4-(3-methylphenyl)-1-piperazinyl)pyridazine; mp. 163.1° C. (compound 203);

3-[4-(3-chlorophenyl)-1-piperazinyl]-6-iodopyridazine; mp. 165.0° C. (compound 204);

3-[4-(2,3-dimethylphenyl)-1-piperazinyl]-6-iodopyridazine; mp. 179.4° C. (compound 205); and 3-iodo-6-[4-[3-(trifluoromethyl)phenyl]-1-piperidinyl]pyridazine; mp. 106.8° C. (compound 206).

Example 30

A mixture of 4.6 parts of 1-[3-(trifluoromethyl)phenyl]piperazine. 6.4 parts of sodium carbonate and 160 parts of 4-methyl-2-pentanone was distilled azeotropically to dry. 3.3 Parts of 3,6-dichloropyridazine were added and the whole was stirred and refluxed for 48 hours using a water separator. After cooling, water was added and the product was extracted with dichloromethane. The organic layer was dried, filtered and evaporated. The residue was purified by column chromatography over silica gel using a mixture of trichloromethane and methanol (99:1 by volume) as eluent. The pure fractions were collected and the eluent was evaporated. The residue was crystallized from 2-propanol, yielding 2.6 parts (37.9%) of 3-chloro-6-[4-[3-(trifluoromethyl)phenyl]-1-piperazinyl]pyridazine; mp. 149.4° C. (compound 207).

Example 31

To a stirred solution of 7.5 parts of 3,6-dichloropyridazine in 75 parts of N,N-dimethylformamide was added dropwise a solution of 8 parts of ethyl 1-piperazinecarboxylate and 5.6 parts of N,N-diethylethanamine in 25 parts of N,N-dimethylformamide. Upon completion, the whole was stirred overnight at a temperature of about 50° C. After cooling, the reaction mixture was poured onto water and the product was extracted with trichloromethane. The organic layer was dried, filtered and evaporated. The residue was crystallized from 2-propanol, yielding 3.6 parts of ethyl 4-(6-chloro-3-pyridazinyl)-1-piperazinecarboxylate; mp. 123.8° C. (compound 208).

Example 32

A mixture of 3.2 parts of 3-chloro-6-(methylsulfonyl)-pyridazine, 3 parts of 1-(3-methylphenyl)piperazine, 2 parts of N,N-diethylethanamine and 180 parts of benzene was stirred for 24 hours at reflux. The reaction mixture was evaporated. Water was added to the residue. The precipitated product was filtered off, washed with water and dissolved in trichloromethane. The solution was dried, filtered and evaporated. The residue was crystallized from methanol. The product was filtered off and dried, yielding 5 parts (89%) of 3-[4-(3-methylphenyl)-1-piperazinyl]-6-(methylsulfonyl)-pyridazine; mp. 201° C. (compound 209).

In a similar manner there were also prepared:

3-[4-(3-methylphenyl)-1-piperazinyl]-6-(methylsulfinyl)pyridazine; mp. 146.9° C. (compound 210);

3-[3,6-dihydro-4-(3-methylphenyl)-1(2H)-Pyridinyl]-6-(methylsulfonyl)pyridazine; mp. 179.8° C. (compound 211); and 3-[3,6-dihydro-4-(3-methylphenyl)-1(2H)-pyridinyl]-6-(methylsulfinyl)pyridazine; mp. 131.0° C. (compound 212).

Example 33

A mixture of 3.3 parts of 3.6-dichloropyridazine, 3.3 parts of 1-(2-pyridinyl)piperazine. 1.5 parts of sodium hydrogencarbonate and 120 parts of ethanol was stirred and refluxed over weekend. The reaction mixture was evaporated. Water was added to the residue and the product was extracted with dichloromethane. The extract was dried, filtered and evaporated. The residue was purified by column chromatography over silica gel using a mixture of trichloromethane and methanol (99:1 by volume) as eluent. The pure fractions were collected and the eluent was evaporated. The residue was crystallized from a mixture of 2-propanol and tetrahydrofuran, yielding 2.5 parts (45.3%) of 3-chloro-6-[4-(2-pyridinyl)-1-piperazinyl]pyridazine; mp. 194.7° C. (compound 213).

Example 34

A mixture of 3.2 parts of 3-chloro-6-(methylthio)-pyridazine, 3.14 parts of 1,2,3,6-tetrahydro-4-(3-methylphenyl)pyridine hydrochloride. 5.3 parts of sodium carbonate and 80 parts of 1-butanol was stirred for 48 hours at reflux temperature. The reaction mixture was evaporated. Water was added. The product was extracted with trichloromethane. The extract was dried, filtered and evaporated. The residue was purified by column chromatography over silica gel using a mixture of trichloromethane and methanol (98:2 by volume) as eluent. The pure fractions were collected and the eluent was evaporated. The residue was crystallized from 2-propanol. The product was filtered off and dried, yielding 0.8 parts (18%) of 3-[3.6-dihydro-4-(3-methylphenyl)-1(2H)-pyridinyl]-6-(methylthio)pyridazine: mp. 129.8° C. (compound 214).

Example 35

To a stirred solution of 300 parts of hexahydro-1H-1,4-diazepine in 900 parts of methylbenzene were added 75 parts of 3,6-dichloropyridazine. The whole was stirred and refluxed for 4 hours. The reaction mixture was evaporated. Water was added to the residue. The product was extracted with trichloromethane. The extract was dried, filtered and evaporated. The residue was converted into the hydrochloride salt in 2-propanol and ethanol. The salt was filtered off and dried, yielding 28 parts (22%) of 1-(6-chloro-3-pyridazinyl)-hexahydro-1H-1,4-diazepine monohydrochloride (compound 215).

In a similar manner there was also prepared:
1-(6-chloro-5-methyl-3-pyridazinyl)hexahydro-1H-1,4-diazepine as a residue (compound 216).

Example 36

A mixture of 3.9 parts of 3,6-dichloro-4,5-dimethyl-pyridazine, 4.2 parts of 1-(2,3-dimethylphenyl)piperazine and 2.94 parts of potassium carbonate was stirred and heated for 4 hours in an oil bath at 190° C. After cooling, the mixture was taken up in water and trichloromethane. The organic layer was separated, dried, filtered and evaporated. The residue was crystallized from 2-propanol. The product was filtered off and dried, yielding 2 parts (30%) of 3-chloro-6-[4-(2.3-dimethylphenyl)-1-piperazinyl]-4,5-dimethylpyridazine; mp. 194.5° C. (compound 217).

In a similar manner there were also prepared:
3-chloro-4,5-dimethyl-6-[4-(3-methylphenyl)-1-piperazinyl]pyridazine; mp. 172.9° C. (compound 218); and
4-(3-methylphenyl)-1-(6-methyl-3-pyridazinyl)-4-piperidinol; mp. 131.5° C. (compound 219).

Example 38

A mixture of 3.5 parts of N-(6-chloro-3-pyridazinyl)acetamide, 3.6 parts of 1-(3-methylphenyl)piperazine and 2.8 parts of potassium carbonate was stirred for 7 hours 1n an oil bath at 160° C. After cooling, trichloromethane and water were added. The layers were separated. The organic layer was dried, filtered and evaporated. The residue was purified by column chromatography over silica gel using a mixture of trichloromethane and methanol (97:3 by volume) as eluent. The second fraction was collected and the eluent was evaporated. The residue was converted into the hydrochloride salt in 2-propanol and 2-propanone. The salt was filtered off and dried, yielding 0.5 parts (6.6%) of 6-4-(3-methylphenyl)-1-piperazinyl]-3-pyridazinamine dihydrochloride; mp. 178.5° C. (compound 220).

Example 38

A mixture of 4 parts of 6-chloro-3-(4-ethylphenoxy)-pyridazine and 6 parts of 1-(3-methylphenyl)piperazine was stirred and heated for 3 hours in an oil bath at 110° C. The whole was allowed to stand overnight. Concentrate ammonium hydroxide and trichloromethane were added. The precipitate was filtered off and the filtrate was purified by column chromatography over silica gel using a mixture of trichloromethane and methanol (95:5 by volume) as eluent. The pure fractions were collected and the eluent was evaporated. The residue was crystallized from 2,2'-oxybispropane. The product was filtered off and dried, yielding 1.7 parts (27%) of 3-(4-ethylphenoxy)-6-[4-(3-methylphenyl)-1-piperazinyl]pyridazine; mp. 106.6° C. (compound 221).

Following the same procedure and using equivalent amounts of the appropriate starting materials, there were also prepared:
3-methyl-6-[4-(3-methylphenyl)-1-piperazinyl]-pyridazine; mp. 152.9° C. (compound 222); and 3-[4-(3-methylphenyl)-1-piperazinyl]-6-(methylthio)-pyridazine; mp. 145.0° C. (compound 223).

Example 39

A mixture of 22 parts of ethyl 4-(6-chloro-5-methyl-3-pyridazinyl}-1-piperazinecarboxylate, 28 parts of potassium hydroxide and 160 parts of 1-butanol was stirred overnight at reflux temperature. The reaction mixture was evaporated. Water was added. The product was extracted with trichloromethane. The extract was dried, filtered and evaporated. 2,2'-Oxybispropane was added. The product was filtered off and dried, yielding 17 parts (100%) of 3-chloro-4-methyl-6-(1-piperazinyl)-pyridazine (compound 224).

Example 40

A mixture of 6 parts of ethyl [1-(6-chloro-3-pyridazinyl)-4-piperidinyl)carbamate and 60 parts of concentrate hydrochloric acid was stirred and refluxed for 24 hours. The reaction mixture was evaporated. Water was added and the whole was treated with concentrate ammonium hydroxide. The product was extracted with trichloromethane. The extract was dried, filtered and evaporated, yielding 3.8 parts (82%) of 1-(6-chloro-3-pyridazinyl)-4-piperidinamine: mp. 260° C. (dec.) (compound 225).

Example 41

A mixture of 3.6 parts of 3-chloro-6-(1-piperazinyl)-pyridazine monohydrochloride, 5.3 parts of sodium carbonate and 90 parts of N,N-dimethylacetamide was stirred for a while at 60° C. Then there were added 3 parts of (3-bromopropyl)benzene and the whole was stirred overnight at 60° C. The reaction mixture was poured into water. The product was filtered off and converted into the hydrochloride salt in 2-propanol. The salt was filtered off and dried, yielding 3.2 parts (60%) of 3-chloro-6-[4-(3-phenylpropyl}-1-piperazinyl]pyridazine monohydrochloride: mp. 207.3° C. (compound 226)

In a similar manner there were also prepared:

3-chloro-4-methyl-6-[4-(3-phenylpropyl)-1-piperazinyl]pyridazine monohydrochloride 1-butanol(1:1).monohydrate; mp. 187.2° C. (compound 227);

3-methoxy-6-[4-(3-phenylpropyl)-1-piperazinyl]-Pyridazine; mp. 78.4° C. (compound 228);

3-[4-(3-phenylpropyl}-1-piperazinyl]pyridazine dihydrochloride. monohydrate: mp. 209.0° C. (compound 229): and 1-acetyl-4-(6-chloro-3-pyridazinyl)piperazine: mp. 153.6° C. (compound 230).

Example 42

A mixture of 3 parts of 3-chloro-6-(1-piperazinyl)-pyridazine. 2 parts of benzeneacetylaldehyde, 1 part of a solution of thiophene in methanol 4% and 200 parts of methanol was hydrogenated at normal pressure and at room temperature with 2 parts of platinum-on-charcoal catalyst 5%. After the calculated amount of hydrogen was taken up, the catalyst was filtered off and the filtrate was evaporated. The residue was crystallized from 2-propanol. The product Was filtered off and dried, yielding 1.5 parts (33%) of 3-chloro-6-[4-(2-phenylethyl)-1-piperazinyl]pyridazine; mp. 140.0° C. (compound 231).

In a similar manner there Were also prepared:

3-(4-butyl-1-piperazinyl)-6-chloropyridazine (E)-2-butenedioate(1:1); mp. 188.2° C. (compound 232);

3-chloro-6-(4-cyclohexyl-1-piperazinyl)pyridazine: mp. 187.2° C (compound 233): and 1-(6-chloro-3-pyridazinyl)-N-(phenylmethyl)-4-piperidinamine: mp. 93.8° C. {compound 234).

Example 43

A mixture of 4 parts of 1-(6-chloro-3-pyridazinyl)-4-(3-methoxyphenyl)-4-piperidinol, 80 parts of ethanol and 50 parts of a hydrochloric acid solution 6N was stirred for 6 hours at reflux temperature. The reaction mixture was evaporated. Water was added and the whole was treated with concentrate ammonium hydroxide. The product was extracted with trichloromethane. The extract was dried, filtered and evaporated. The residue was crystallized from 2-propanol. The product was filtered off and dried, yielding 2.5 parts (64%) of 3-chloro-6-[3,6-dihydro-4-(3-methoxyphenyl)-1(2H)-pyridinyl]pyridazine; mp. 126.4° C. (compound 235).

Following the same procedure and using equivalent amounts of the appropriate starting materials, there were also prepared:

3-chloro-6-[4-(3-chlorophenyl)-3,6-dihydro-1(2H)-pyridinyl]-pyridazine: mp. 133.9° C. (compound 236):

3-chloro-6-(3,4-dihydro-5-phenyl-1(2H)-pyridinyl)-pyridazine; mp. 146.0° C. (compound 237);

3-chloro-6-[3,4-dihydro-5-(3-methylphenyl)-1(2H)-pyridinyl]pyridazine: mp. 160.0° C. (compound 238):

3-chloro-6-[4-(3-fluorophenyl)-3,6-dihydro-1(2H)-pyridinyl]pyridazine; mp. 124.7° C. (compound 239);

3-chloro-6-[4-(2,3-dimethylphenyl)-3,6-dihydro-1(2H)-pyridinyl]-pyridazine; mp. 144.2° C. (compound 240);

3-chloro-6-[4-(3-chlorophenyl)-3,6-dihydro-5-methyl-1(2H)-pyridinyl]-pyridazine; mp. 88.5° C. (compound 241);

3-chloro-6-[3,4-dihydro-5-[3-(trifluoromethyl)-phenyl]-1(2H)-pyridinyl]pyridazine; mp. 163.2° C. (compound 242);

3-chloro-6-[3,6-dihydro-5-[3-(trifluoromethyl)-phenyl]-1(2H)-pyridinyl]pyridazine; mp. 112.5° C. (compound 243);

3-chloro-6-[5-(3-fluorophenyl)-3.6-dihydro-1(2H)-pyridinyl]pyridazine; mp. 134.9° C. (compound 244);

3-chloro-6-[3,4-dihydro-5-(3-methoxyphenyl)-1(2H)-pyridinyl]-pyridazine; mp. 129.1° C. (compound 245);

3-chloro-6-[5-(2,3-dimethylphenyl)-3,4-dihydro-1(2H)-pyridinyl]-pyridazine; mp. 148.8° C. (compound 246);

3-chloro-6-[3.6-dihydro-4-(2-naphthalenyl)-1(2H)-pyridinyl]pyridazine monohydrochloride hemihydrate; mp. 187.2° C. (compound 247);

3-chloro-6-[3-(3-methylphenyl)-2H-pyrrol-1(5H)-yl]pyridazine; mp. 198.1° C. (compound 248);

3-chloro-6-[2,3-dihydro-4-(3-methylphenyl)-1H-pyrrol-1-yl]pyridazine; mp. 195.3° C. (compound 249);

3-chloro-6-[3,6-dihydro-4-(2-phenylethyl)-1(2H)-pyridinyl]pyridazine: mp. 104.2° C. (compound 250);

3-chloro-6-[5-[4-chloro-3-(trifluoromethyl)phenyl]-3,4-dihydro-1(2H)pyridinyl]pyridazine; mp. 140.9° C. (compound 251);

3-chloro-6-[3-(3-fluorophenyl)-2,3-dihydro-1H-pyrrol-1-yl]pyridazine; mp. 213.0° C. (compound 252);

3-chloro-6-[3-(3-fluorophenyl)-2,5-dihydro-1H-pyrrol-1-yl]pyridazine; mp. 228.8° C. (compound 253);

3-[3,6-dihydro-4-(3-methylphenyl)-1(2H)-pyridinyl]-6-methylpyridazine; mp. 123.4° C. (compound 254);

3-[3,6-dihydro-4-(3-methylphenyl)-1(2H)-pyridinyl]-6-methoxypyridazine; mp. 116.4° C. (compound 255); and 3-butoxy-6-[3,6-dihydro-4-(3-methylphenyl)-1(2H)-pyridinyl]pyridazine; mp. 97.8° C. (compound 256).

Example 44

To a stirred mixture of 80 parts of 1-butanol, 0.4 parts of sodium hydroxide and 0.94 parts of phenol were added 2.2 parts of 3-chloro-6-[4-(3-methylphenyl)-1-piperazinyl]pyridazine at 60° C. The whole was stirred and refluxed over weekend. The reaction mixture was evaporated. The residue was crystallized from 2,2'-oxybispropane. The product was filtered off and dried, yielding 2 parts (64%) of 3-butoxy-6-[4-(3-methylphenyl)-1-piperazinyl]pyridazine: mp. 105.2° C. (compound 257).

Example 45

To a stirred sodium methoxide solution, previously prepared starting from 1.6 parts of sodium in 24 parts of methanol, were added 4 parts of 3-chloro-6-[4-(3-methylphenyl)-1-piperazinyl]pyridazine. The whole was stirred and refluxed for 40 hours. After cooling 25 parts of water were added. The product was filtered off, washed with water and dissolved in trichloromethane. The organic layer was dried, filtered and evaporated. The residue was crystallized from a mixture of 2-propanol and 2,2'-oxybispropane. The product was filtered off and dried, yielding 2 parts (50%) of 3-methoxy-6-[4-(3-methylphenyl)-1-piperazinyl]pyridazine; mp. 137.1° C. (compound 258).

Following the same procedure and using equivalent amounts of the appropriate starting materials, there were also prepared:

3-[4-(3-fluorophenyl)-3,4-dihydro-1(2H)-pyridinyl]-6-methoxypyridazine; mp. 85.2° C. (compound 259);

3-[3,6-dihydro-4-(2,3-dimethylphenyl)-1(2H)-pyridinyl]-6-methoxypyridazine; mp. 110.8° C. (compound 260);

1-(6-methoxy-3-pyridazinyl)-4-(3-methylphenyl)-4-piperidinol; mp. 125.6° C. (compound 261);

3-[3,4-dihydro-4-(3-methylphenyl)-1(2H)-pyridinyl]-6-ethoxypyridazine; mp. 84.3° C. (compound 262); and 1-(6-butoxy-3-pyridazinyl)-4-(3-methylphenyl)-4-piperidinol: mp. 106 7° C. (compound 263).

Example 46

A mixture of 1.9 parts of phenol. 2.9 parts of 3-chloro-6-[4-(3-methylphenyl)-1-piperazinyl]pyridazine and 2.76 parts of potassium carbonate was stirred and heated for 7 hours in an oil bath at 150° C. After cooling, water was added. The product was extracted with trichloromethane. The extract was dried, filtered and evaporated. The residue was crystallized from a mixture of 2-propanol and 2,2'-oxybispropane. The product was filtered off and dried, yielding 2 parts (60%) of 3-[4-(3-methylphenyl)-1-piperazinyl]-6-phenoxypyridazine; mp. 123.4° C. (compound 264).

In a similar manner there were also prepared:

3-(4-chlorophenoxy)-6-[4-(3-methylphenyl)-1-piperazinyl]pyridazine; mp. 130.1° C. (compound 265); and 3-[4-(3-methylphenyl)-1-piperazinyl]-6-(phenylthio)-pyridazine; mp. 135.3° C. (compound 266).

Example 47

To a stirred solution of 0.7 parts of sodium in 20 parts of benzenemethanol were added 5.8 parts of 3-chloro-6-[4-(3-methylphenyl)-1-piperazinyl]pyridazine. The whole was stirred and heated in an oil bath at 180° C. After standing overnight, water was added and the product was extracted with trichloromethane. The extract was dried, filtered and evaporated. 2,2'-Oxybispropane was added to the residue. The product was filtered off and crystallized from a mixture of 2-propanol and methanol. The product was filtered off and dried, yielding 3.4 parts (47%) of 3-[4-(3-methylphenyl)-1-piperazinyl]-6-(phenylmethoxy)pyridazine: mp. 159.4° C. (compound 267).

In a similar manner there was also prepared:

4-(3-methylphenyl)-1-[6-(phenylmethoxy}-3-pyridazinyl]-4-piperidinol: mp. 124.8° C. (compound 268).

Example 48

A mixture of 6.1 parts of 4-(3-methylphenyl)-1-[6-(phenylmethoxy)-3-pyridazinyl]-4-piperidinol and 250 parts of 2-methoxyethanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was boiled in 2-propanol. The product was filtered off and dried, yielding 4.5 parts (97%) of 6-[4-hydroxy-4-(3-methylphenyl)-1-piperidinyl]-3-pyridazinol; mp. 264.6° C. (compound 269).

A mixture of 2.9 parts of 6-[4-hydroxy-4-(3-methylphenyl)-1-piperidinyl]-3-pyridazinol, 30 parts of a hydrochloric acid solution 6N and 24 parts of ethanol was stirred for 2 hours at reflux temperature. The reaction mixture was evaporated. Crushed ice was added and the whole was treated with concentrate ammonium hydroxide. The product was extracted with trichloromethane. The extract was dried, filtered and evaporated. The residue was purified by column chromatography over silica gel using a mixture of trichloromethane and methanol (98:2 by volume) as eluent. The pure fractions were collected and the eluent was evaporated. The residue was crystallized from a mixture of 2-propanol and 2.2'-oxybispropane. The product was filtered off and dried, yielding 2 parts (75%) of 6-[3,6-dihydro-4-(3-methylphenyl)-1(2H)-pyridinyl]-3-pyridazinol; mp. 179.0° C. (compound 270).

Example 49

A mixture of 6 parts of 3-[4-(3-methylphenyl)-1-piperazinyl)-6-(phenylmethoxy)pyridazine and 60 parts of concentrate hydrochloric acid was stirred and refluxed for 3 hours. The whole was allowed to stand overnight and treated With concentrate ammonium hydroxide. The product was filtered off, washed with water and dissolved in trichloromethane. The organic layer was dried, filtered and evaporated. The residue was crystallized from a mixture of 2-propanol and 2.2'-oxybispropane. The product was filtered off and dried, yielding 4.5 parts (98%) of 6-[4-(3-methylphenyl)-1-piperazinyl]-3(2H)-pyridazinone; mp. 209.8° C. (compound 271).

Example 50

A mixture of 7.3 Parts of 3-chloro-6-[4-(4-methoxyphenyl)-1-piperazinyl]pyridazine, 2 parts of calcium oxide and 200 parts of methanol was hydrogenated at normal pressure and at room temperature with 2 parts of palladium-on-charcoal catalyst 10%. After the calculated amount of hydrogen was taken up, the catalyst was filtered off over Hyflo and the filtrate was evaporated. The residue was crystallized from 2-propanol, yielding 4.1 parts (63.2%) of 3-[4-(4-methoxyphenyl)-1-piperazinyl]pyridazine; mp. 133.4° C. (compound 272).

Example 51

A mixture of 5.8 parts of 3-chloro-6-[4-(3-methylphenyl)-1-piperazinyl]pyridazine and 3 parts of thiourea was stirred for 3 hours in an oil bath at 165° C. After cooling, there were added 150 parts of a sodium hydroxide solution 0.5N. The whole was stirred and refluxed for 15 minutes. It was filtered while hot and the filtrate was neutralized with acetic acid. The product was filtered off, washed with water and separated by column chromatography over silica gel using a mixture of trichloromethane and methanol (98.5:1.5 by volume) as eluent. The pure fractions were collected and the eluent was evaporated. The residue was crystallized from a mixture of ethanol and tetrahydrofuran. The product was filtered off and dried, yielding 1.3 parts (22.7%) of 6-[4-(3-methylphenyl)-1-piperazinyl]-3-pyridazinethiol; mp. 174.2° C. (compound 273).

Example 52

To a stirred solution of 0.92 parts of sodium in 8 parts of methanol were added 45 parts of benzene. Methanol was distilled off and then 6.2 parts of methyl 6-[4-(3-methylphenyl)-1-piperazinyl]-3-pyridazinecarboxylate and 3.5 parts of ethyl acetate in 45 parts of benzene were added. The whole was stirred and refluxed overnight. The reaction mixture was evaporated. 100 Parts of water were added. The mixture was acidified with 24 parts of concentrate hydrochloric acid, boiled for 2 hours, cooled and treated with sodium hydrogen carbonate. The product was filtered off, washed with water and dissolved in trichloromethane. The solution was dried, filtered and evaporated. The residue was purified by column chromatography over silica gel using a mixture of trichloromethane and methanol (98:2 by volume) as eluent. The pure fractions were collected and the eluent was evaporated. The residue was crystallized from a mixture of 2-propanol and 2,2'-oxybispropane. The product was filtered off and dried, yielding 3 parts (51%) of 1-[6-[4-(3-methylphenyl)-1-piperazinyl]-3-pyridazinyl]ethanone; mp. 135.9° C. (compound 274).

In a similar manner there Were also prepared:
1-[6-[3,6-dihydro-4-(3-methylphenyl)-1(2H)-pyridinyl]-3-pyridazinyl]-ethanone: mp. 115.0° C. (compound 275).

C. Pharmacological Examples

Example 53

In order to illustrate the useful anti-viral properties of the compounds of the present invention a number of such compounds were tested in the previously described Rhinovirus Cythopatic Effect Test. These compounds together with the results of the test are gathered in the following table.

| Compound No. | lowest concentration in μg/ml |
| --- | --- |
| 5 | 10 |
| 8 | 10 |
| 29 | 0.4 |
| 207 | 0.4 |
| 149 | 0.4 |
| 213 | 2 |
| 34 | 0.08 |
| 35 | 2 |
| 36 | 0.4 |
| 37 | 2 |
| 40 | 0.016 |
| 41 | 0.4 |
| 44 | 0.4 |
| 48 | 10 |
| 10 | 2 |
| 136 | 0.003 |
| 26 | 0.4 |
| 11 | 2 |
| 25 | 2 |
| 15 | 2 |
| 16 | 10 |
| 18 | 0.4 |
| 21 | 2 |
| 56 | 0.4 |
| 57 | 2 |
| 58 | 0.016 |
| 257 | 10 |
| 22 | 0.08 |
| 24 | 2 |
| 146 | 0.4 |
| 23 | 0.016 |
| 60 | 0.016 |
| 61 | 0.08 |
| 148 | 0.08 |
| 63 | 0.016 |
| 64 | 0.4 |
| 203 | 0.003 |
| 161 | 10 |
| 66 | 2 |
| 67 | 10 |
| 69 | 0.4 |
| 218 | 0.4 |
| 165 | 0.08 |
| 166 | 10 |
| 77 | 0.08 |
| 168 | 0.003 |
| 170 | 2 |
| 80 | 0.04 |
| 204 | 0.003 |
| 266 | 10 |
| 83 | 2 |
| 171 | 10 |
| 202 | 0.016 |
| 84 | 0.016 |
| 172 | 2 |
| 173 | 2 |
| 258 | 0.0006 |
| 142 | 0.016 |
| 143 | 0.0006 |
| 174 | 2 |
| 86 | 10 |
| 28 | 0.0006 |
| 175 | 0.0006 |
| 88 | 0.003 |
| 89 | 0.4 |
| 90 | 0.016 |
| 91 | 0.4 |
| 236 | 0.016 |
| 93 | 0.08 |
| 96 | 0.4 |
| 238 | 2 |
| 101 | 0.4 |
| 104 | 2 |
| 222 | 0.08 |
| 223 | 0.08 |
| 241 | 0.016 |
| 145 | 0.003 |
| 231 | 10 |
| 112 | 0.08 |
| 210 | 2 |
| 113 | 10 |
| 209 | 10 |

-continued

| Compound No. | lowest concentration in µg/ml |
|---|---|
| 247 | 0.4 |
| 274 | 10 |
| 120 | 2 |
| 250 | 0.4 |
| 273 | 0.08 |
| 259 | 0.08 |
| 126 | 2 |
| 212 | 2 |
| 275 | 2 |

D. Composition Examples

"Active ingredient" (A.I.) as used throughout the following examples relates to a compound of formula (I), a possible stereochemically isomeric form or pharmaceutically acceptable acid addition salt thereof.

Example 54: Oral Drops

500 Grams of the A.I. was dissolved in 0.5 liters of 2-hydroxypropanoic acid and 1.5 liters of the polyethylene glycol at 60°-80° C. After cooling to 30°-40° C. there were added 35 liters of polyethylene glycol and the mixture was stirred well. Then there was added a solution of 1750 grams of sodium saccharin in 2.5 liters of purified water and while stirring there were added 2.5 liters of cocoa flavor and polyethylene glycol q.s. to a volume of 50 liters, providing an oral drop solution comprising 10 milligrams of the A.I. per milliliter. The resulting solution was filled into suitable containers.

Example 55: Oral Solution

9 Grams of methyl 4-hydroxybenzoate and 1 gram of propyl 4-hydroxybenzoate were dissolved in 4 liters of boiling purified water. In 3 liters of this solution were dissolved first 10 grams of 2.3-dihydroxybutanedioic acid and thereafter 20 grams of the A.I. The latter solution was combined with the remaining part of the former solution and 12 liters 1,2,3-propanetriol and 3 liters of sorbitol 70% solution were added thereto. 40 Grams of sodium saccharin were dissolved in 0.5 liters of water and 2 milliliters of raspberry and 2 milliliters of gooseberry essence were added. The latter solution was combined with the former, water was added q.s. to a volume of 20 liters providing an oral solution comprising 20 milligrams of the active ingredient per teaspoonful (5 milliliters). The resulting solution was filled in suitable containers.

Example 56: Capsules

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelating capsules, comprising each 20 milligrams of the active ingredient.

Example 57: Film-coated Tablets

Preparation of Tablet Core

A mixture of 100 grams of the A.I, 570 grams lactose and 200 grams starch was mixed well and thereafter humidified with a solution of 5 grams sodium dodecyl sulfate and 10 grams polyvinylpyrrolidone in about 200 milliliters of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 milligrams of the active ingredient.

Coating

To a solution of 10 grams methyl cellulose in 75 milliliters of denaturated ethanol there was added a solution of 5 grams of ethyl cellulose in 150 milliliters of dichloromethane. Then there were added 75 milliliters of dichloromethane and 2.5 milliliters 1,2,3-propanetriol. 10 Grams of polyethylene glycol was molten and dissolved in 75 milliliters of dichloromethane. The latter solution was added to the former and then there were added 2.5 grams of magnesium octadecanoate, 5 grams of polyvinylpyrrolidone and 30 milliliters of concentrated colour suspension (Opaspray K-1-2109) and the whole was homogenated.

The tablet cores were coated with the thus obtained mixture in a coating apparatus.

Example 58: Injectable Solution 1.8 Grams methyl 4-hydroxybenzoate and 0.2 grams propyl 4-hydroxybenzoate were dissolved in about 0.5 liters of boiling water for injection. After cooling to about 50° C. there were added while stirring 4 grams lactic acid. 0.05 propylene glycol and 4 grams of the A.I. The solution was cooled to room temperature and supplemented with water for injection q.s. ad 1 liter volume, giving a solution of 4 milligrams A.I. per milliliters. The solution was sterilized by filtration (U.S.P. XVII p. 811) and filled in sterile containers.

Example 59: Suppositories

3 Grams A.I. was dissolved in a solution of 3 grams 2,3-dihydroxybutanedioic acid in 25 milliliters polyethylene glycol 400. 12 Grams surfactant and triglycerides q.s. ad 300 grams were molten together. The latter mixture was mixed well with the former solution. The thus obtained mixture was poured onto moulds at a temperature of 37°-38° C. to form 100 suppositories each containing 30 milligrams of the active ingredient.

What is claimed is:

1. A compound of the formula:

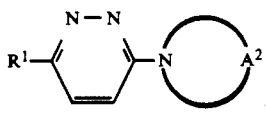

a pharmaceutically acceptable acid-addition salt or a stereoisomeric form or a tautomeric form thereof, wherein:

$R^1$ is a member selected from the group consisting of hydrogen, halo, 1H-imidazol-1-yl, lower alkyloxy, aryloxy, aryllower alkyloxy, lower alkylthio, arylthio, hydroxy, mercapto, amino, lower alkylsulfinyl, lower alkylsulfonyl, cyano, lower alkyloxycarbonyl, lower alkylcarbonyl, and lower alkyl; and $A^2$ is a bivalent radical of the formula:

$$-C_mH_{2m}-C(R^5)(R^6)-C_nH_{2n}- \qquad (c); \text{ or}$$

$$-C_{m-1}H_{2(m-1)}-C(R^7)=C(R^8)-C_nH_{2n}- \qquad (d);$$

wherein one of the hydrogen atoms within the radical $C_mH_{2m}$, $C_{m-1}H_{2(m-1)}$, or $C_nH_{2n}$ may be replaced by lower alkyl or aryl;

m is the integer 1 or 2 and n is the integer 2;

$R^5$ is hydrogen, aryl, arylamino, (aryl)(lower alkyl)amino, hydroxy, or indolyl;

$R^6$ is hydrogen, aryl, arylcarbonyl, or (arylcarbonyl)lower alkyl; and $R^7$ and $R^8$ are, each independently, members selected from the group consisting of hydrogen, lower alkyl, aryl, aryllower alkyl, and pyridinyl;

wherein aryl is phenyl, being optionally substituted with up to 3 substituents, each independently selected from the group consisting of halo, lower alkyl, trifluoromethyl, nitro, amino, lower alkyloxy, hydroxy and lower alkyloxycarbonyl; thienyl; and naphthalenyl, provided that when $A^2$ is a radical of formula (c) and one of $R^5$ and $R^6$ is hydrogen, then the other of $R^5$ and $R^6$ cannot be hydrogen, hydroxy, or lower alkyl.

2. A compound according to claim 1 wherein $R^1$ is halo, lower alkyloxy, aryloxy, lower alkylthio, arylthio, or cyano.

3. A compound according to claim 1, wherein $R^1$ is halo.

4. A compound according to claim 3 wherein said compound is selected from the group consisting of 3-chloro-6-[3,6-dihydro-4-(3-methylphenyl)-1(2H)-pyridinyl]pyridazine and the pharmaceutically acceptable acid addition salts thereof.

5. An anti-rhinoviral composition consisting essentially of an inert carrier and as an active ingredient an anti-rhinovirally effective amount of a compound of the formula:

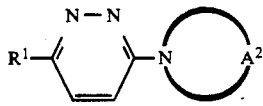

a pharmaceutically acceptable acid-addition salt or a stereoisomeric form or a tautomeric form thereof, wherein:

$R^1$ is a member selected from the group consisting of hydrogen, halo, 1H-imidazol-1-yl, lower alkyloxy, aryloxy, aryllower alkyloxy, lower alkylthio, arylthio, hydroxy, mercapto, amino, lower alkylsulfinyl, lower alkylsulfonyl, cyano, lower alkyloxycarbonyl, lower alkylcarbonyl, and lower alkyl; and $A^2$ is a bivalent radical of the formula:

$$-C_mH_{2m}-C(R^5)(R^6)-C_nH_{2n}- \quad (c); \text{ or}$$

$$-C_{m-1}H_{2(m-1)}-C(R^7)=C(R^8)-C_nH_{2n}- \quad (d);$$

wherein one of the hydrogen atoms within the radical $C_mH_{2m}$, $C_{m-1}H_{2(m-1)}$, or $C_nH_{2n}$ may be replaced by lower alkyl or aryl;

m is the integer 1 or 2 and n is the integer 2;

$R^5$ is hydrogen, aryl, arylamino, (aryl)(lower alkyl)amino, hydroxy, or indolyl;

$R^6$ is hydrogen, aryl, arylcarbonyl, or (arylcarbonyl)lower alkyl; and $R^7$ and $R^8$ are, each independently, members selected from the group consisting of hydrogen, lower alkyl, aryl, aryllower alkyl, and pyridinyl;

wherein aryl is phenyl, being optionally substituted with up to 3 substituents, each independently selected from the group consisting of halo, lower alkyl, trifluoromethyl, nitro, amino, lower alkyloxy, hydroxy and lower alkyloxycarbonyl; thienyl; and naphthalenyl, provided that when $A^2$ is a radical of formula (c) and one of $R^5$ and $R^6$ is hydrogen, then the other of $R^5$ and $R^6$ cannot be hydrogen, hydroxy, or lower alkyl.

6. The anti-rhinoviral composition of claim 5 wherein $R^1$ is halo, lower alkyloxy, aryloxy, lower alkylthio, arylthio, or cyano.

7. The anti-rhinoviral composition of claim 5, wherein $R^1$ is halo.

8. The anti-rhinoviral composition of claim 7 wherein said compound is selected from the group consisting of 3-chloro-6-[3,6-dihydro-4-(3-methylphenyl)-1(2H)-pyridinyl]pyridazine and the pharmaceutically acceptable acid addition salts thereof.

* * * * *